United States Patent
Zentgraf

(10) Patent No.: US 12,426,874 B2
(45) Date of Patent: *Sep. 30, 2025

(54) MINIMALLY INVASIVE REPAIR OF A VALVE LEAFLET IN A BEATING HEART

(71) Applicant: NeoChord, Inc., Maple Grove, MN (US)

(72) Inventor: John Zentgraf, Minneapolis, MN (US)

(73) Assignee: NeoChord, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/429,694

(22) Filed: Feb. 1, 2024

(65) Prior Publication Data

US 2024/0245396 A1 Jul. 25, 2024

Related U.S. Application Data

(63) Continuation of application No. 17/892,843, filed on Aug. 22, 2022, now Pat. No. 11,911,023, which is a
(Continued)

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0482* (2013.01); *A61B 17/29* (2013.01);
(Continued)

(58) Field of Classification Search
CPC ...... A61B 2090/3614; A61B 2090/306; A61B 2090/0807; A61B 2017/2926;
(Continued)

(56) References Cited

U.S. PATENT DOCUMENTS 2,751,908 A 6/1956 Wallace
3,664,330 A 5/1972 Deutsch
(Continued)

FOREIGN PATENT DOCUMENTS

EP 1039851 B1 7/2005
EP 1637091 A2 3/2006
(Continued)

OTHER PUBLICATIONS

Application and File History for U.S. Appl. No. 13/898,709, filed May 21, 2013, now U.S. Pat. No. 9,364,213. Inventors: Speziali.
(Continued)

*Primary Examiner* — Jocelin C Tanner
(74) *Attorney, Agent, or Firm* — Merchant & Gould P.C.

(57) ABSTRACT

A device for performing minimally invasive repair of mitral valve leaflets in a beating heart through the delivery and implantation of artificial chordae tendineae includes a handle for positioning the device into a chest cavity of the patient, a capture assembly adapted to capture a valve leaflet between distal an proximal tip portions, a needle adapted to penetrate the valve leaflet, and a capture confirmation system for verifying capture of the valve leaflet between the distal and proximal tip portions.

20 Claims, 27 Drawing Sheets

Related U.S. Application Data continuation of application No. 16/678,571, filed on Nov. 8, 2019, now Pat. No. 11,419,602, which is a continuation of application No. 14/310,069, filed on Jun. 20, 2014, now Pat. No. 10,507,018, which is a continuation of application No. 12/254,807, filed on Oct. 20, 2008, now Pat. No. 8,758,393.

(60) Provisional application No. 60/999,873, filed on Oct. 22, 2007, provisional application No. 60/999,635, filed on Oct. 19, 2007, provisional application No. 60/999,431, filed on Oct. 18, 2007.

(51) Int. Cl.
*A61B 17/06* (2006.01)
*A61B 17/29* (2006.01)
*A61B 90/00* (2016.01)

(52) U.S. Cl.
CPC ............... *A61B 2017/00243* (2013.01); *A61B 2017/06042* (2013.01); *A61B 2017/2926* (2013.01); *A61B 2090/3614* (2016.02)

(58) Field of Classification Search
CPC ........... A61B 2017/06042; A61B 2017/00243; A61B 17/29; A61B 17/0482; A61B 17/0469
USPC ......................................................... 606/144
See application file for complete search history.

(56) References Cited

U.S. PATENT DOCUMENTS

| | | |
|---|---|---|
| 3,667,474 A | 6/1972 | Lapkin et al. |
| 3,842,840 A | 10/1974 | Schweizer |
| 4,258,716 A | 3/1981 | Sutherland |
| 4,351,345 A | 9/1982 | Carney |
| 4,759,348 A | 7/1988 | Cawood |
| 4,935,027 A | 6/1990 | Yoon |
| 4,957,498 A | 9/1990 | Caspari et al. |
| 4,960,424 A | 10/1990 | Grooters |
| 4,972,874 A | 11/1990 | Jackson |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth et al. |
| 5,336,229 A | 8/1994 | Noda |
| 5,336,231 A | 8/1994 | Adair |
| 5,373,877 A | 12/1994 | Chapman |
| 5,383,877 A | 1/1995 | Clarke |
| 5,431,666 A | 7/1995 | Sauer et al. |
| 5,452,733 A | 9/1995 | Sterman et al. |
| 5,474,519 A | 12/1995 | Bloomer |
| 5,547,455 A | 8/1996 | McKenna et al. |
| 5,571,215 A | 11/1996 | Sterman et al. |
| 5,601,578 A | 2/1997 | Murphy |
| 5,626,607 A | 5/1997 | Malecki et al. |
| 5,653,716 A | 8/1997 | Malo et al. |
| 5,665,096 A | 9/1997 | Yoon |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,741,276 A | 4/1998 | Poloyko et al. |
| 5,741,277 A | 4/1998 | Gordon et al. |
| 5,762,458 A | 6/1998 | Wang et al. |
| 5,762,613 A | 6/1998 | Sutton et al. |
| 5,769,791 A | 6/1998 | Benaron et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,857,961 A | 1/1999 | Vanden Hoek et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr. et al. |
| 5,972,004 A | 10/1999 | Williamson, IV et al. |
| 5,972,020 A | 10/1999 | Carpentier et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr. et al. |
| 6,050,936 A | 4/2000 | Schweich, Jr. et al. |
| 6,053,933 A | 4/2000 | Balazs et al. |
| 6,059,715 A | 5/2000 | Schweich, Jr. et al. |
| 6,077,214 A | 6/2000 | Mortier et al. |
| 6,117,114 A | 9/2000 | Paradis |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr. et al. |
| 6,162,233 A | 12/2000 | Williamson, IV et al. |
| 6,165,119 A | 12/2000 | Schweich, Jr. et al. |
| 6,165,120 A | 12/2000 | Schweich, Jr. et al. |
| 6,165,183 A | 12/2000 | Kuehn et al. |
| 6,178,346 B1 | 1/2001 | Amundson et al. |
| 6,183,411 B1 | 2/2001 | Mortier et al. |
| 6,190,357 B1 | 2/2001 | Ferrari et al. |
| 6,197,053 B1 | 3/2001 | Cosgrove et al. |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,270,508 B1 | 8/2001 | Klieman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund et al. |
| 6,619,291 B2 | 9/2003 | Htavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | Goar et al. |
| 6,629,921 B1 | 10/2003 | Schweich, Jr. et al. |
| 6,629,984 B1 | 10/2003 | Chan |
| 6,645,205 B2 | 11/2003 | Ginn |

(56) References Cited

U.S. PATENT DOCUMENTS

| | | |
|---|---|---|
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,716,224 B2 | 4/2004 | Singhatat |
| 6,718,985 B2 | 4/2004 | Hlavka et al. |
| 6,723,038 B1 | 4/2004 | Schroeder et al. |
| 6,733,509 B2 | 5/2004 | Nobles et al. |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,083 B2 | 8/2004 | Seguin |
| 6,770,084 B1 | 8/2004 | Bain et al. |
| 6,793,618 B2 | 9/2004 | Schweich, Jr. et al. |
| 6,802,860 B2 | 10/2004 | Cosgrove et al. |
| 6,808,488 B2 | 10/2004 | Mortier et al. |
| 6,810,882 B2 | 11/2004 | Langberg et al. |
| 6,840,246 B2 | 1/2005 | Downing |
| 6,858,003 B2 | 2/2005 | Evans et al. |
| 6,875,224 B2 | 4/2005 | Grimes |
| 6,893,448 B2 | 5/2005 | O'Quinn et al. |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,465,500 B2 | 6/2013 | Speziali |
| 8,469,974 B2 | 6/2013 | Skinlo et al. |
| 8,758,393 B2 | 6/2014 | Zentgraf |
| 8,968,338 B2 | 3/2015 | Speziali |
| 9,192,374 B2 | 11/2015 | Zentgraf |
| 9,314,242 B2 | 4/2016 | Bachman |
| 9,364,213 B2 | 6/2016 | Speziali |
| 10,507,018 B2 | 12/2019 | Zentgraf |
| 11,911,023 B2 * | 2/2024 | Zentgraf ............ A61B 17/0469 |
| 2001/0005787 A1 | 6/2001 | Oz et al. |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0029080 A1 | 3/2002 | Mortier et al. |
| 2002/0049402 A1 | 4/2002 | Peacock, III et al. |
| 2002/0077524 A1 | 6/2002 | Schweich, Jr. et al. |
| 2002/0169359 A1 | 11/2002 | McCarthy et al. |
| 2002/0173694 A1 | 11/2002 | Mortier et al. |
| 2002/0183766 A1 | 12/2002 | Seguin |
| 2003/0004562 A1 | 1/2003 | Dicarlo |
| 2003/0032979 A1 | 2/2003 | Mortier et al. |
| 2003/0050529 A1 | 3/2003 | Vidlund et al. |
| 2003/0050693 A1 | 3/2003 | Quijano et al. |
| 2003/0078600 A1 | 4/2003 | O'Quinn et al. |
| 2003/0105519 A1 | 6/2003 | Fasol et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. et al. |
| 2003/0167071 A1 | 9/2003 | Martin et al. |
| 2003/0171641 A1 | 9/2003 | Schweich, Jr. et al. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | Goldfarb et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama et al. |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0243229 A1 | 12/2004 | Vidlund et al. |
| 2004/0267083 A1 | 12/2004 | McCarthy et al. |
| 2005/0004668 A1 | 1/2005 | Aklog et al. |
| 2005/0021055 A1 | 1/2005 | Toubia et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0044365 A1 | 2/2005 | Haukka et al. |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich et al. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove et al. |
| 2005/0216039 A1 | 9/2005 | Lederman |
| 2005/0222589 A1 | 10/2005 | Chu |
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0069304 A1 | 3/2006 | Takemoto et al. |

(56) References Cited

U.S. PATENT DOCUMENTS

| | | |
|---|---|---|
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0127509 A1 | 6/2006 | Eckman et al. |
| 2006/0135993 A1 | 6/2006 | Seguin |
| 2006/0149123 A1 | 7/2006 | Vidlund et al. |
| 2006/0161040 A1 | 7/2006 | McCarthy et al. |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0220275 A1 | 10/2006 | Varner |
| 2006/0241340 A1 | 10/2006 | Schroeder et al. |
| 2006/0287657 A1 | 12/2006 | Bachman |
| 2007/0002627 A1 | 1/2007 | Youn |
| 2007/0027451 A1 | 2/2007 | Desinger et al. |
| 2007/0049952 A1* | 3/2007 | Weiss ............... A61B 17/0218 606/144 |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy et al. |
| 2007/0118154 A1 | 5/2007 | Crabtree |
| 2007/0118155 A1 | 5/2007 | Goldfarb et al. |
| 2007/0129737 A1 | 6/2007 | Goldfarb et al. |
| 2007/0179511 A1 | 8/2007 | Paolitto et al. |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0027468 A1 | 1/2008 | Fenton, Jr. et al. |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold et al. |
| 2008/0091264 A1 | 4/2008 | Machold et al. |
| 2008/0097482 A1 | 4/2008 | Bain et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2008/0188873 A1 | 8/2008 | Speziali |
| 2008/0195200 A1 | 8/2008 | Vidlund et al. |
| 2008/0208006 A1 | 8/2008 | Farr |
| 2008/0228223 A1* | 9/2008 | Alkhatib ............ A61B 17/0401 606/221 |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0131880 A1 | 5/2009 | Speziali et al. |
| 2009/0131956 A1 | 5/2009 | Dewey et al. |
| 2009/0156995 A1 | 6/2009 | Martin et al. |
| 2009/0163934 A1 | 6/2009 | Raschdorf, Jr. et al. |
| 2009/0259304 A1 | 10/2009 | O'Beirne et al. |
| 2010/0042147 A1 | 2/2010 | Janovsky et al. |
| 2010/0174297 A1 | 7/2010 | Speziali |
| 2011/0066165 A1 | 3/2011 | Skinlo et al. |
| 2014/0039324 A1 | 2/2014 | Speziali |
| 2014/0364875 A1 | 12/2014 | Zentgraf |
| 2015/0148821 A1 | 5/2015 | Speziali |

FOREIGN PATENT DOCUMENTS

| | | |
|---|---|---|
| EP | 1845861 A2 | 10/2007 |
| EP | 1408850 B1 | 9/2009 |
| EP | 1845861 A4 | 12/2009 |
| JP | H06142114 A | 5/1994 |
| WO | 9900059 A1 | 1/1999 |
| WO | 9930647 A1 | 6/1999 |
| WO | 0006026 A2 | 2/2000 |
| WO | 0006027 A2 | 2/2000 |
| WO | 0006028 A1 | 2/2000 |
| WO | 0016700 A1 | 3/2000 |
| WO | 0166018 A1 | 9/2001 |
| WO | 0006026 A3 | 11/2001 |
| WO | 0195809 A1 | 12/2001 |
| WO | 03001893 A2 | 1/2003 |
| WO | 03059209 A2 | 7/2003 |
| WO | 03082157 A2 | 10/2003 |
| WO | 03059209 A3 | 11/2003 |
| WO | 2004021893 A1 | 3/2004 |
| WO | 2004043265 A2 | 5/2004 |
| WO | 2005039428 A2 | 5/2005 |
| WO | 2005039428 A3 | 6/2005 |
| WO | 2005094525 A2 | 10/2005 |
| WO | 2006032051 A2 | 3/2006 |
| WO | 2006065966 A2 | 6/2006 |
| WO | 2006078694 A2 | 7/2006 |
| WO | 2006116310 A2 | 11/2006 |
| WO | 2006127509 A2 | 11/2006 |
| WO | 2007002627 A1 | 1/2007 |
| WO | 2007027451 A2 | 3/2007 |
| WO | 2006116310 A3 | 5/2007 |
| WO | 2007062128 A2 | 5/2007 |
| WO | 2007081418 A1 | 7/2007 |
| WO | 2007062128 A3 | 10/2007 |
| WO | 2007117612 A1 | 10/2007 |
| WO | 2008010738 A2 | 1/2008 |
| WO | 2009052528 A2 | 4/2009 |
| WO | 2006065966 A3 | 5/2009 |

OTHER PUBLICATIONS

Application and File History for U.S. Appl. No. 14/614,570, filed Feb. 5, 2015. Inventors: Speziali.

Application and File history for U.S. Appl. No. 11/813,695, filed Jul. 11, 2007, now U.S. Pat. No. 8,465,500. Inventors: Speziali.

Application and File history for U.S. Appl. No. 12/254,807, filed Oct. 20, 2008, now U.S. Pat. No. 8,758,393. Inventors: Zentgraf.

Application and File history for U.S. Appl. No. 12/254,808, filed Oct. 20, 2008, now U.S. Pat. No. 9,192,374. Inventors: Zentgraf.

Application and File history for U.S. Appl. No. 12/709,220, filed Feb. 19, 2010, now U.S. Pat. No. 8,968,338. Inventors: Speziali.

Application and File history for U.S. Appl. No. 14/310,069, filed Jun. 20, 2014, now U.S. Pat. No. 10,507,018. Inventors: Zentgraf.

EP Application No. 06718728.6, Extended EP Search Report dated Nov. 11, 2009, 7 pages.

EP Application No. 08839048.9, EP Search Report dated Sep. 16, 2010, 7 pages.

Interactive Cardio Vascular and Thoracic Surgery; Abstracts; Suppl 3 to vol. Sep. 7, 2008 52 pages.

Machine translation of JP 06142114.

PCT International Preliminary Report on Patentability/Written Opinion for PCT/US2008/080560, dated Apr. 20, 2010, 6 pages.

PCT/US2006/01699, Search Report and Written Opinion dated May 6, 2008, 5 pages.

PCT/US2008/080560, Search Report & Written Opinion dated Aug. 24, 2009, 9 pages.

Port Access System for Mitral Valve Repair Proves Its Value in Study; MedGadget Jul. 9, 2009 (2 pages).

* cited by examiner

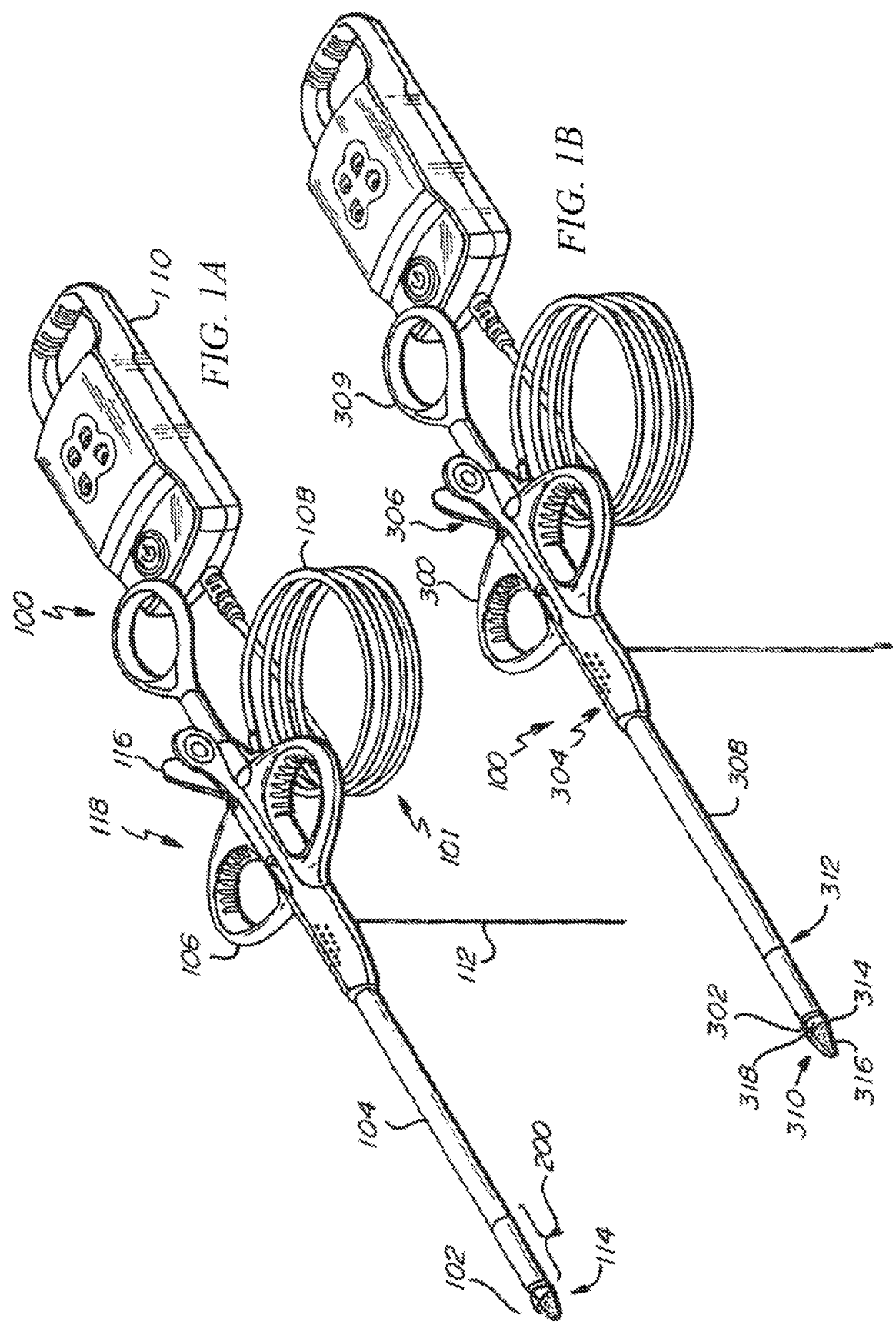

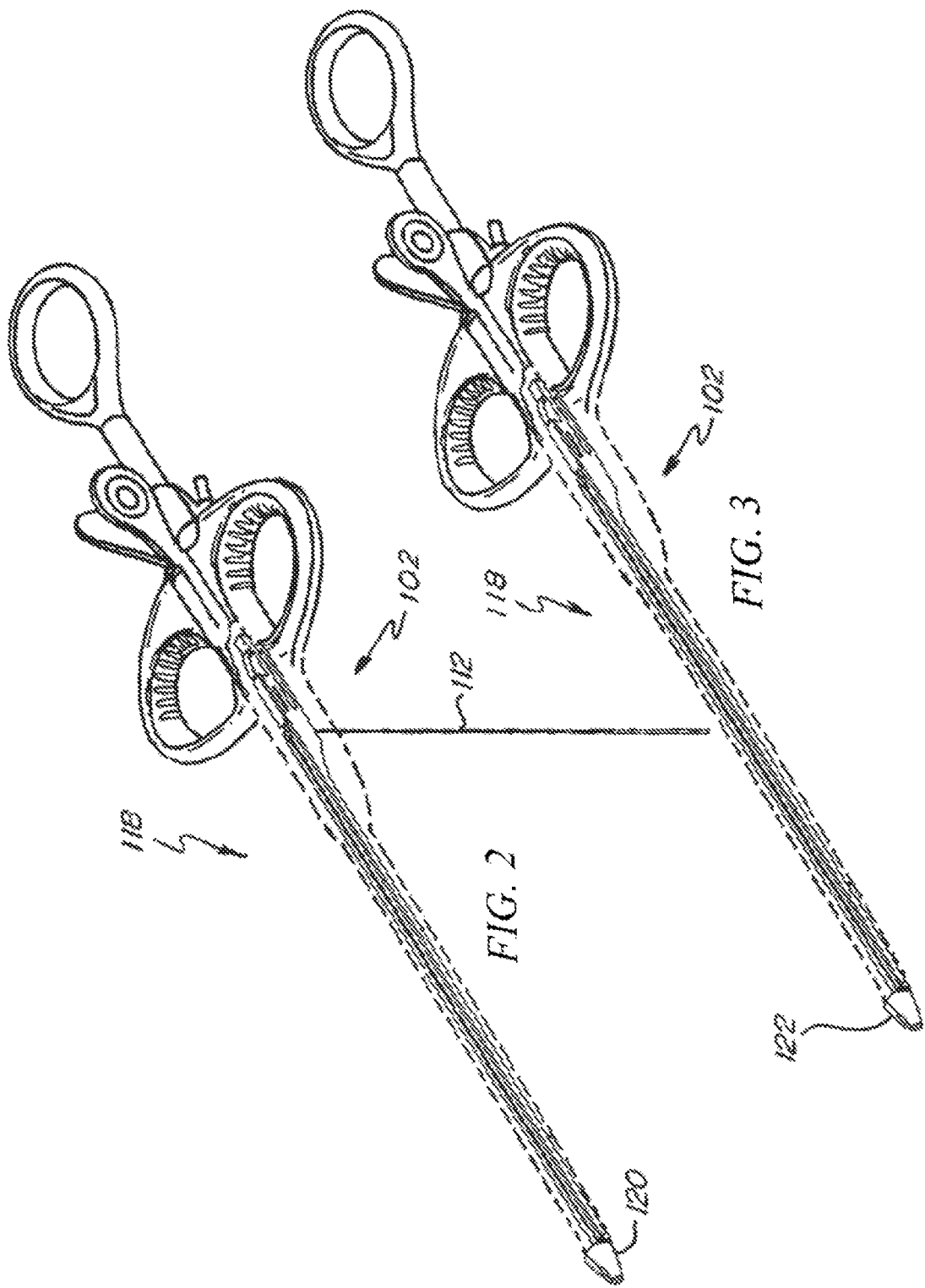

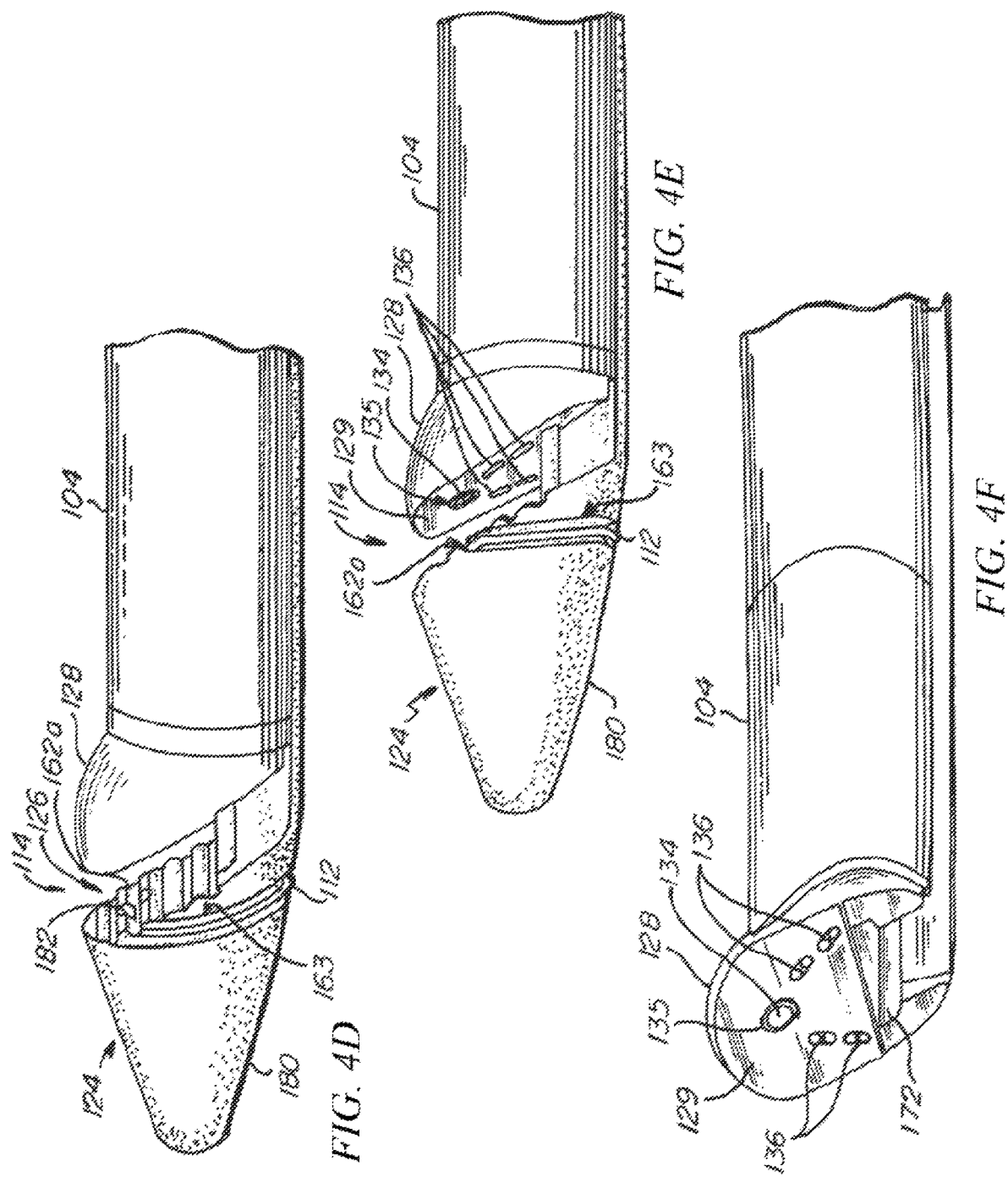

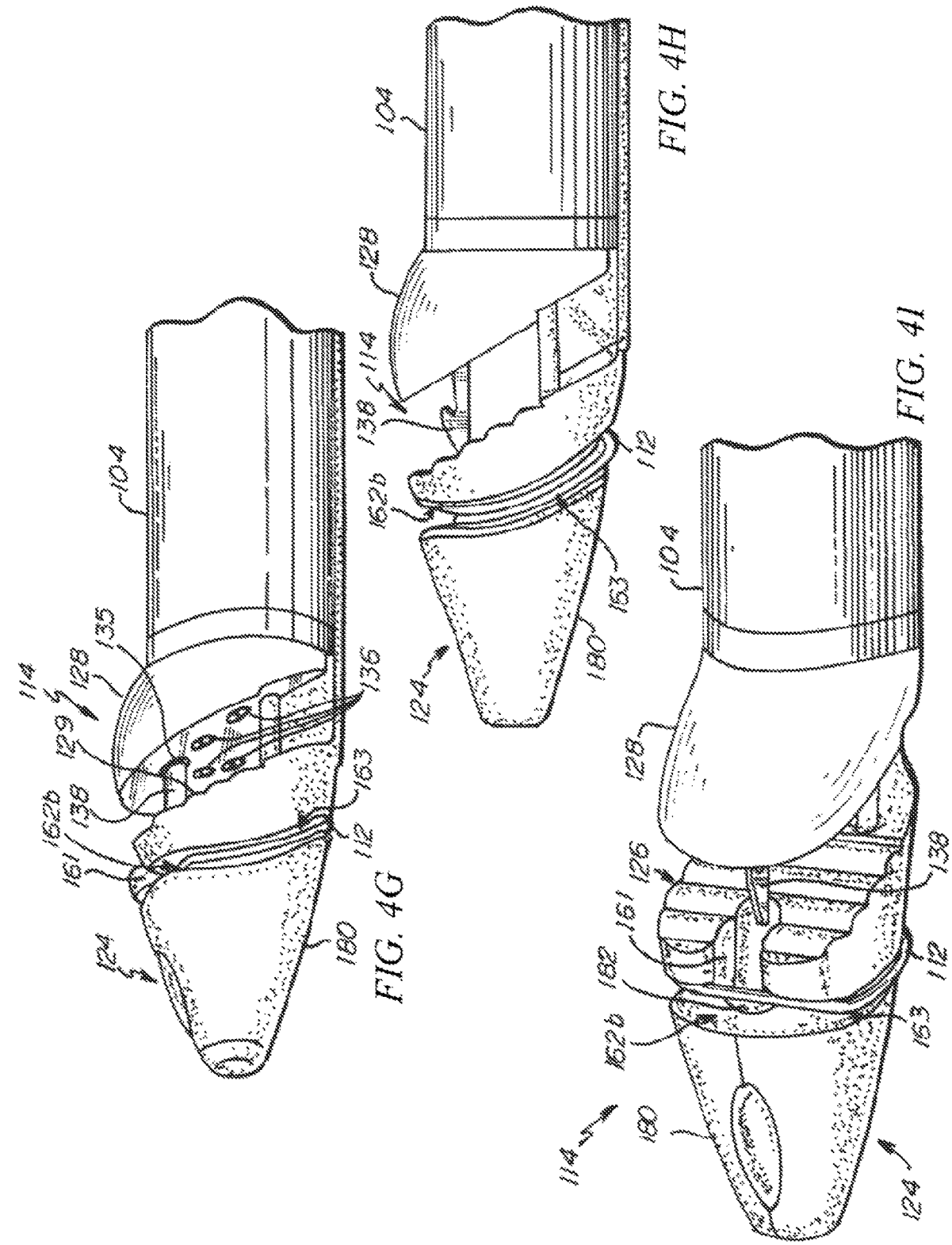

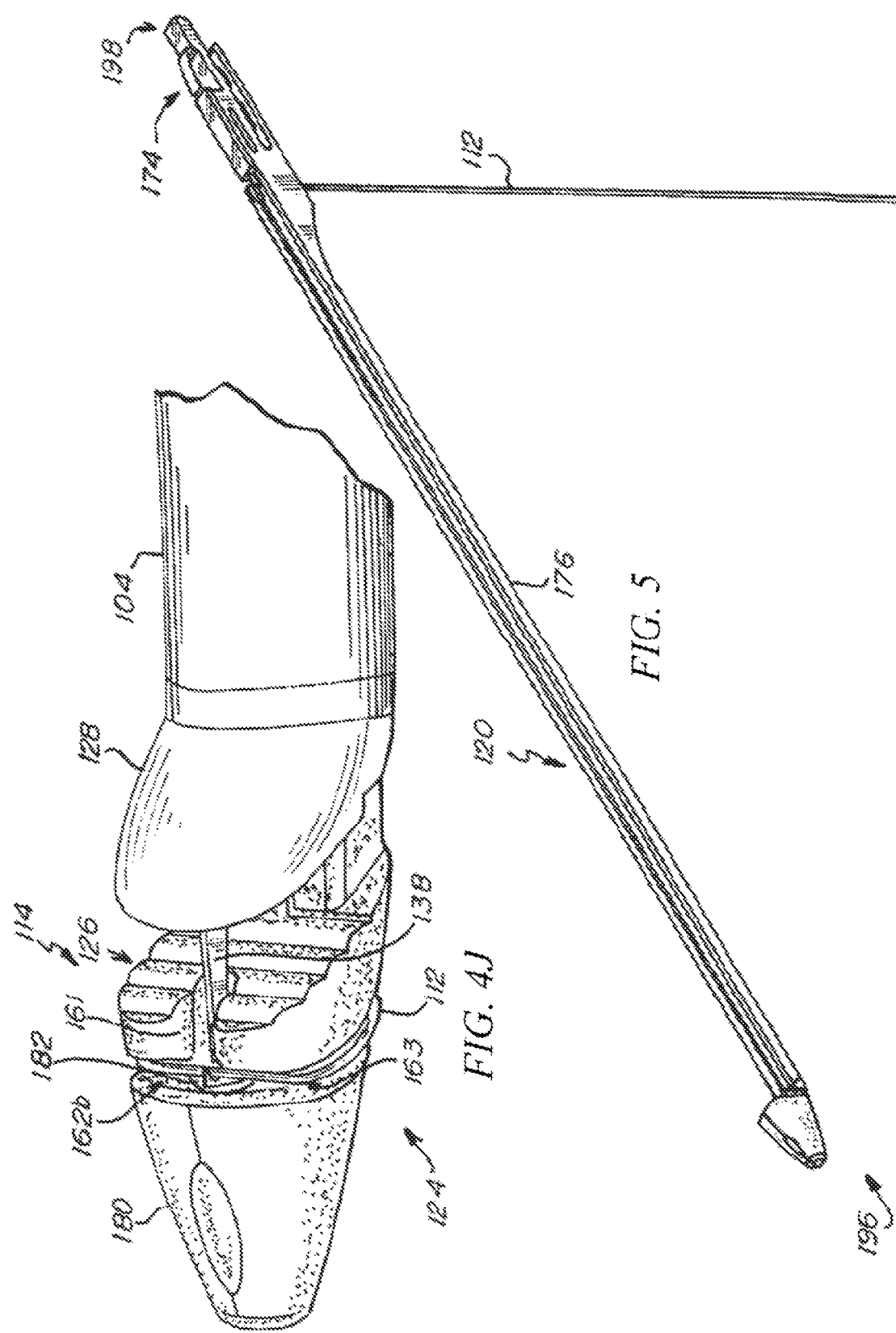

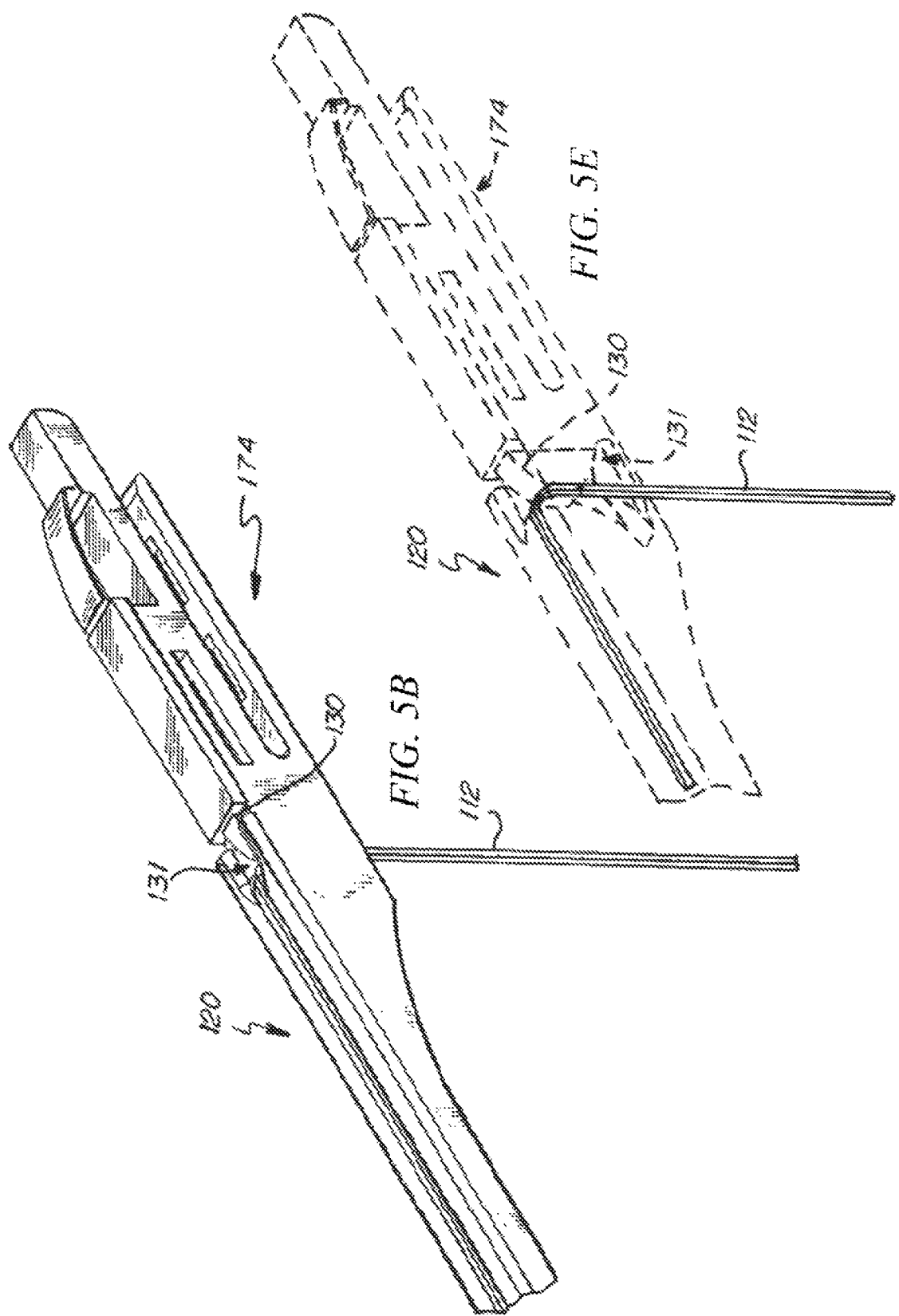

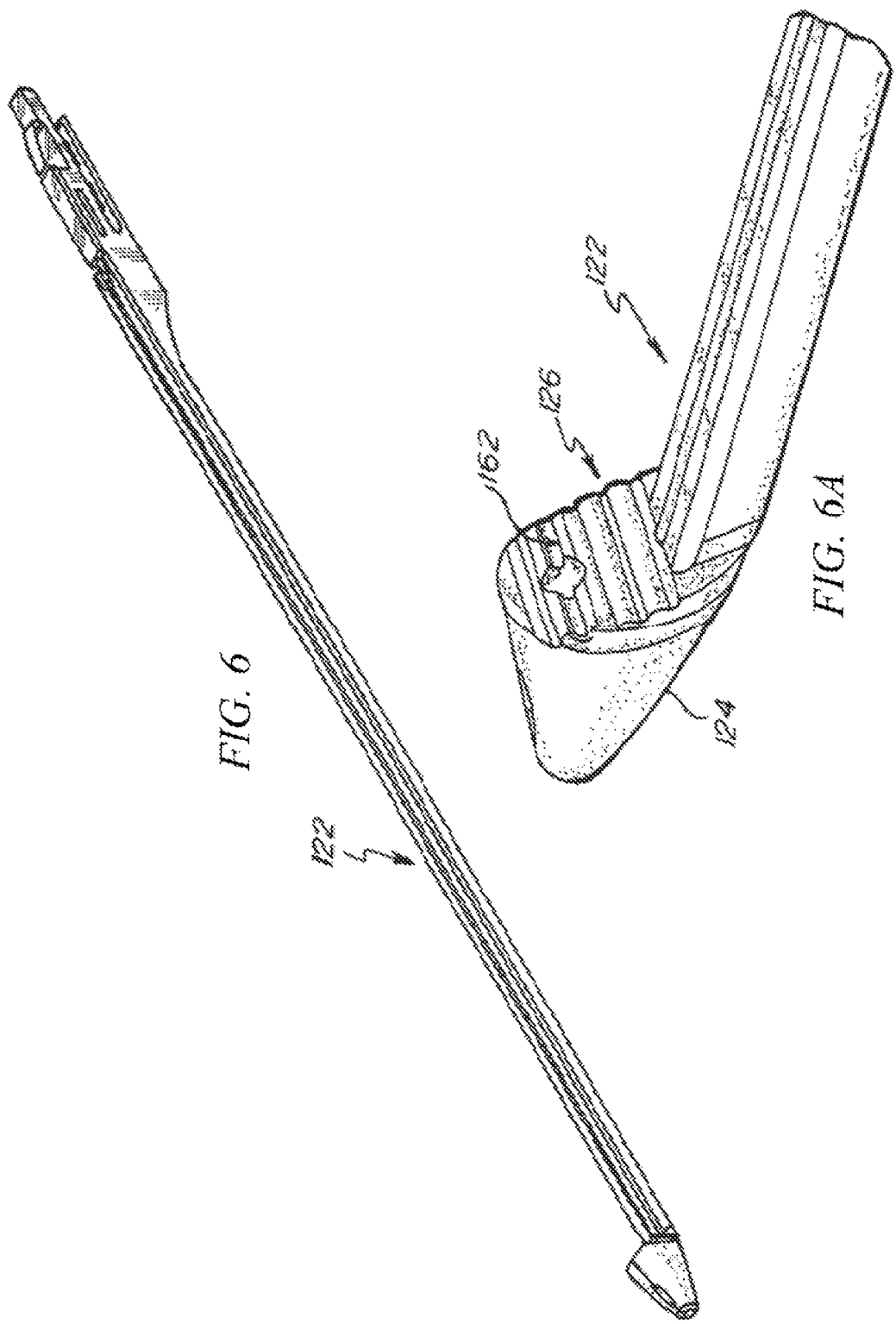

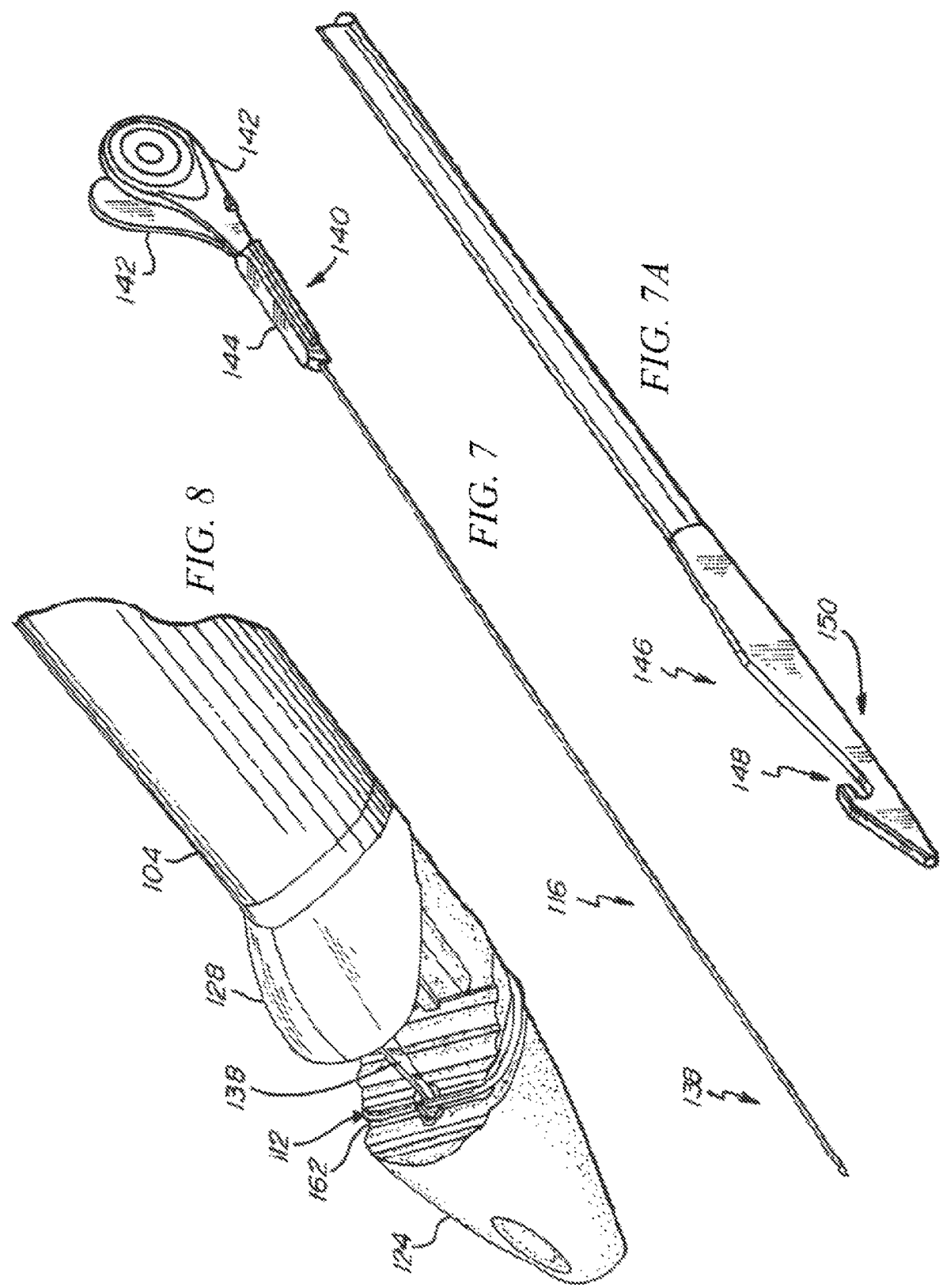

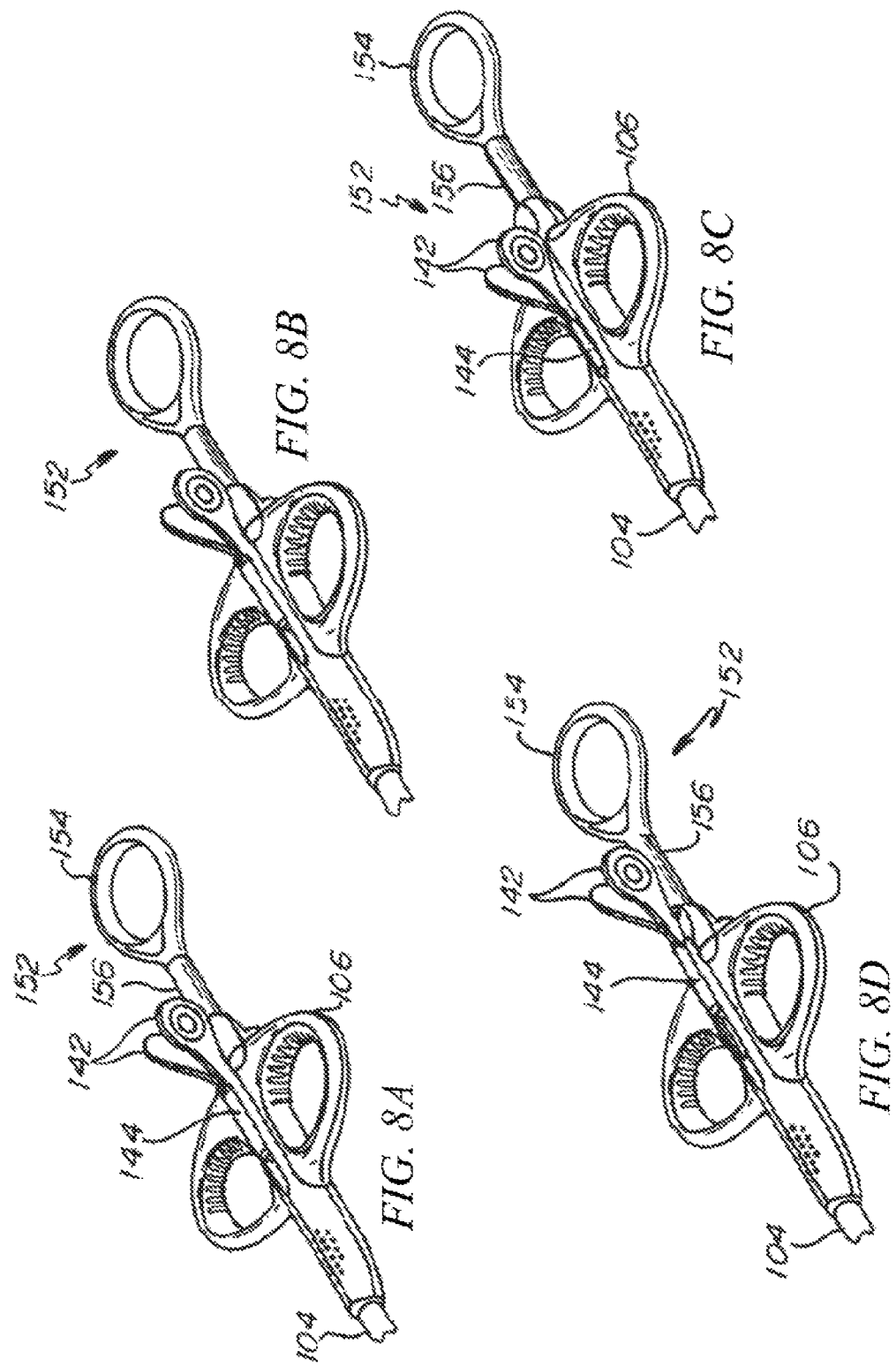

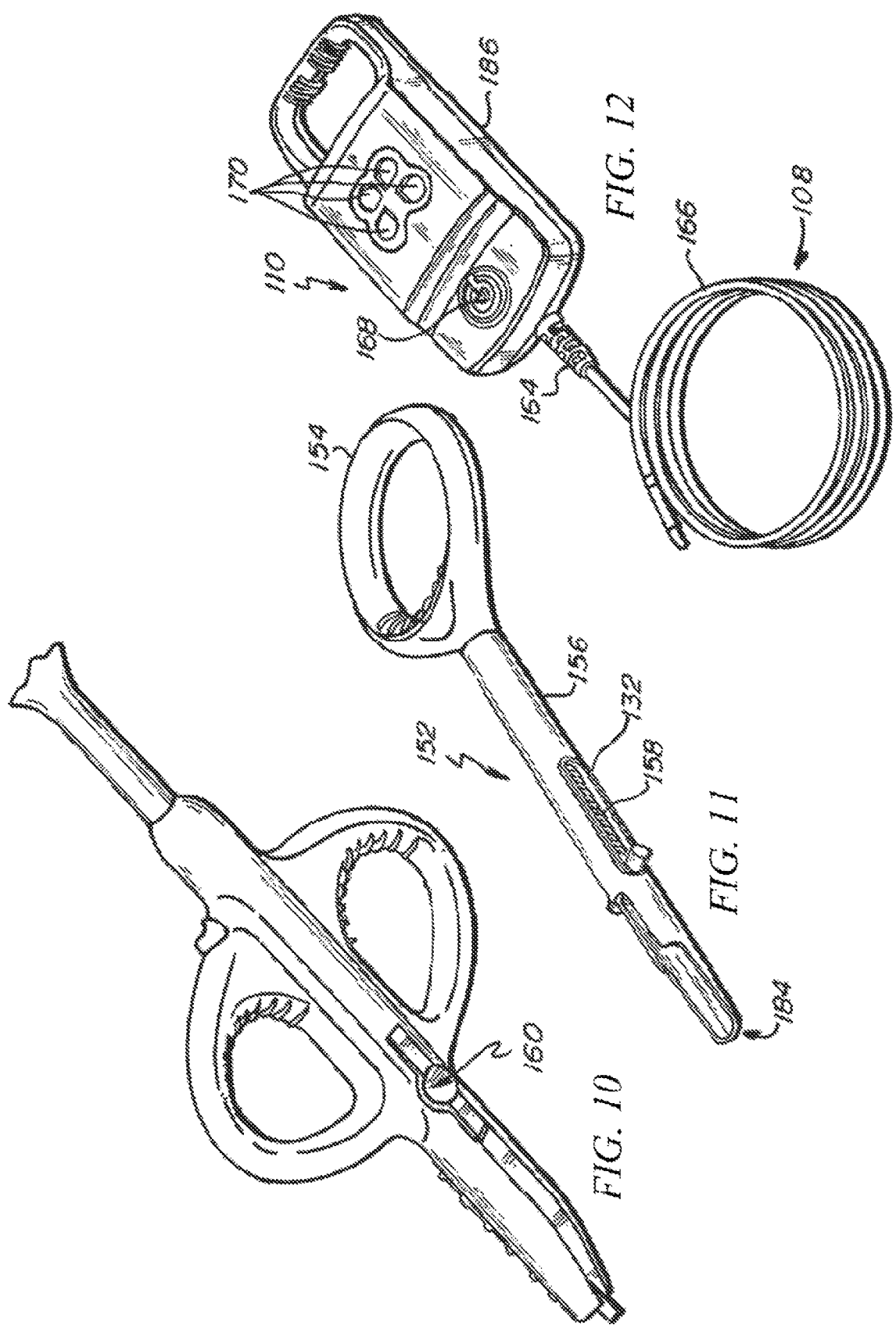

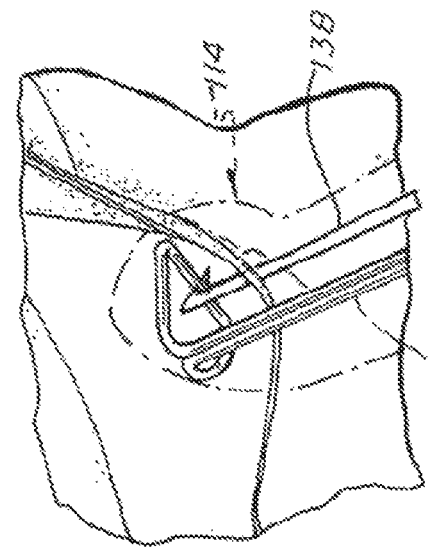
FIG. 26
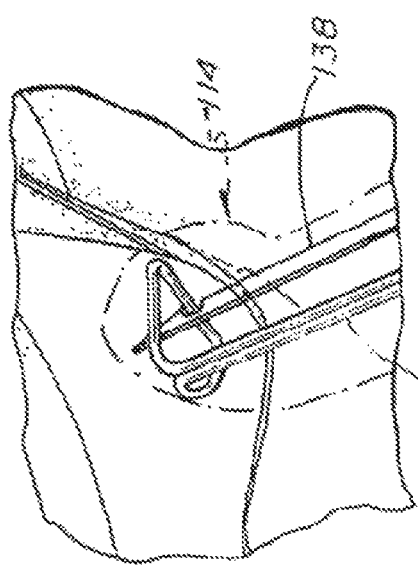
FIG. 27
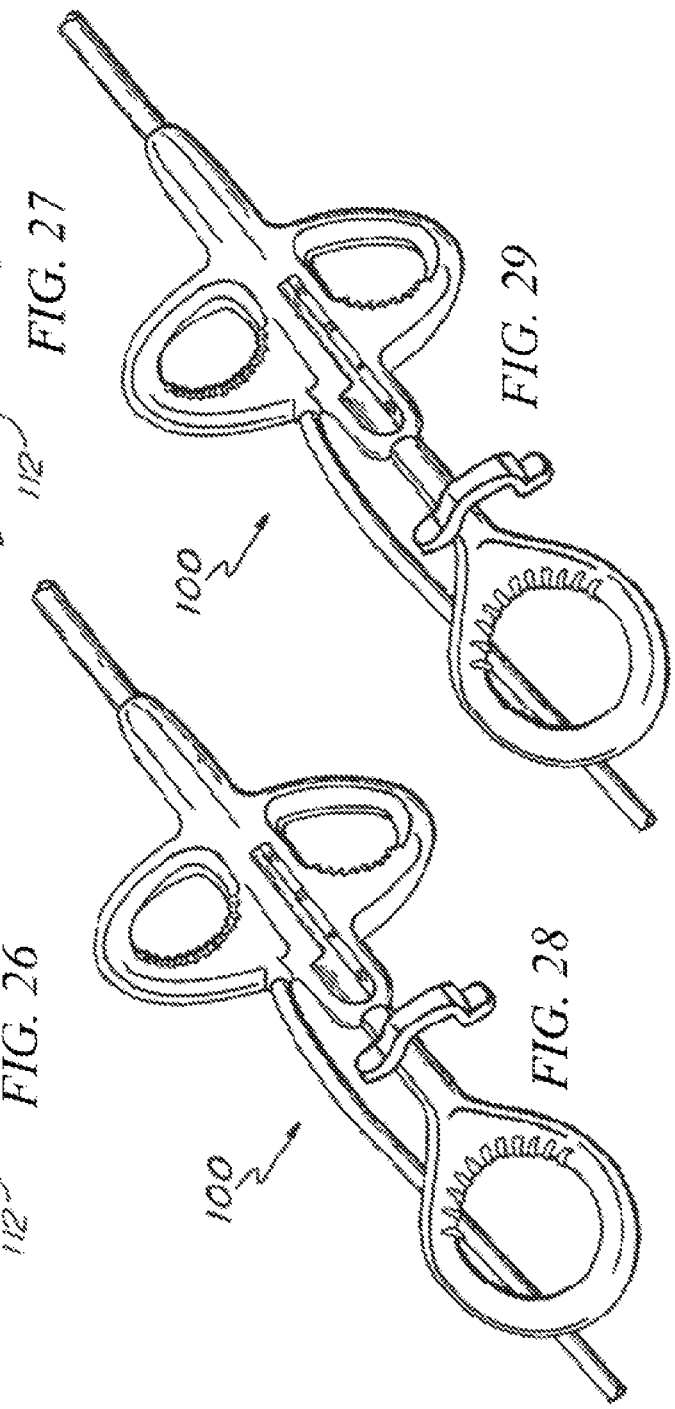
FIG. 28
FIG. 29

TEE confirms MR reduction (NOT TO SCALE)

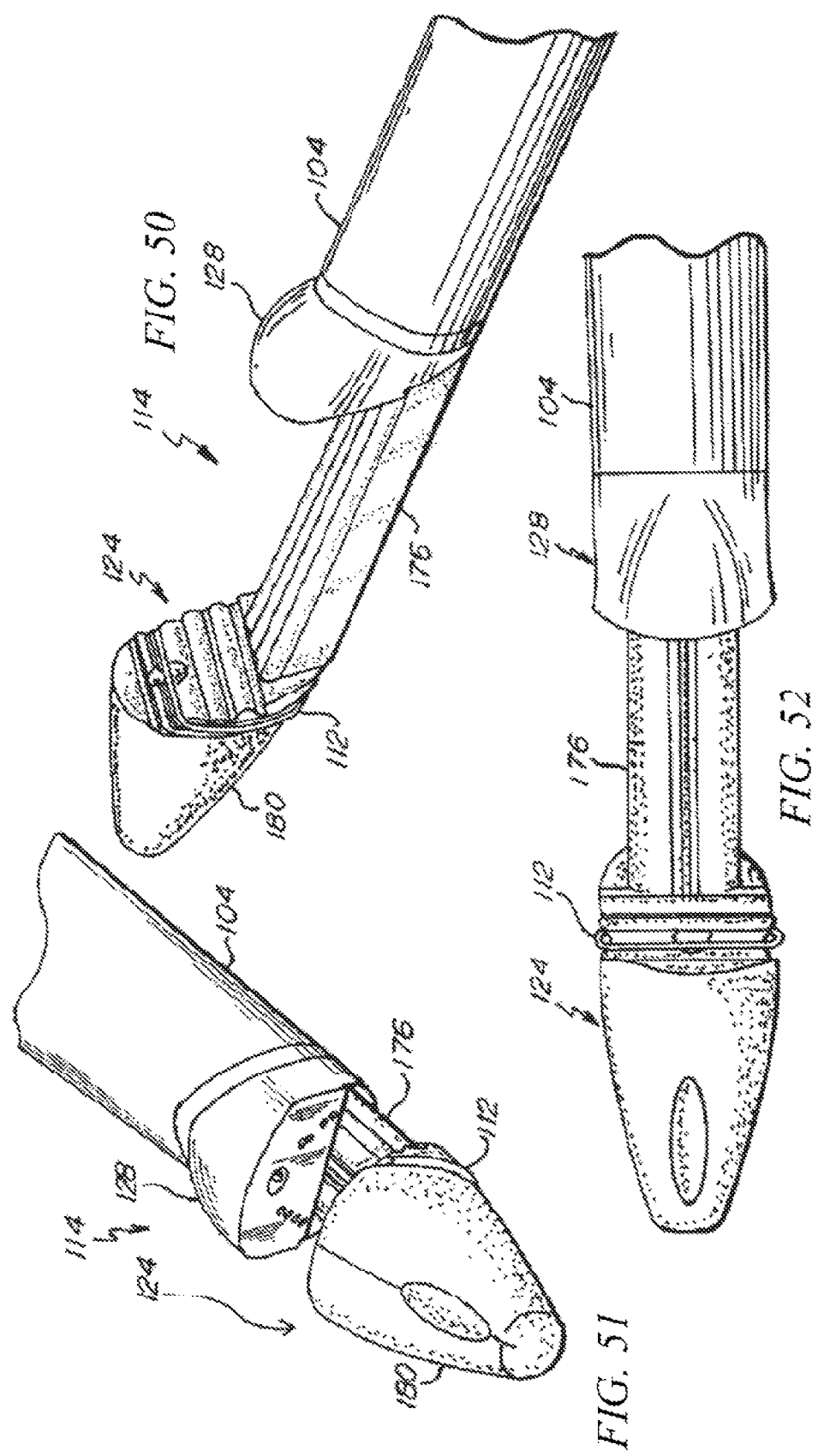

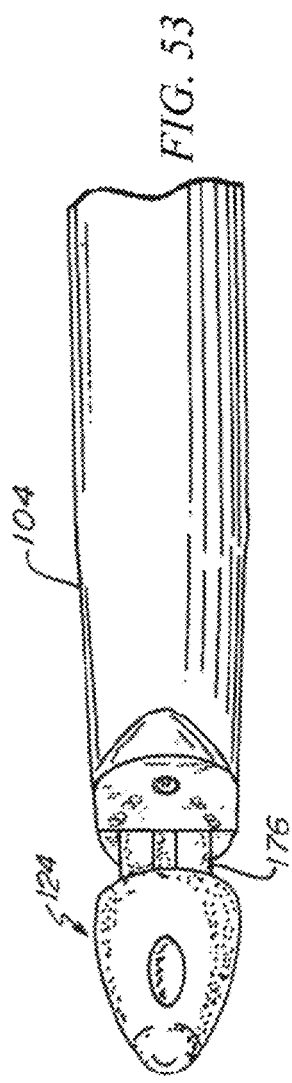
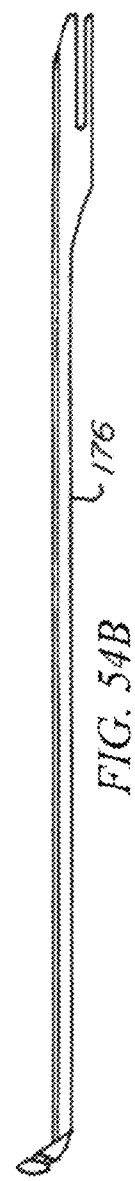
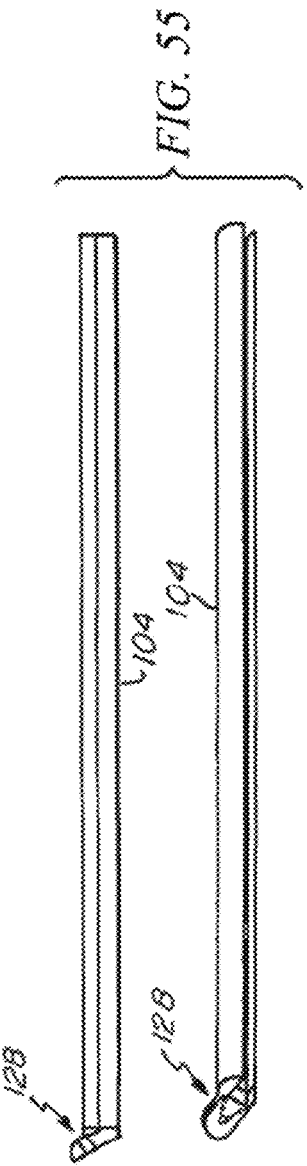
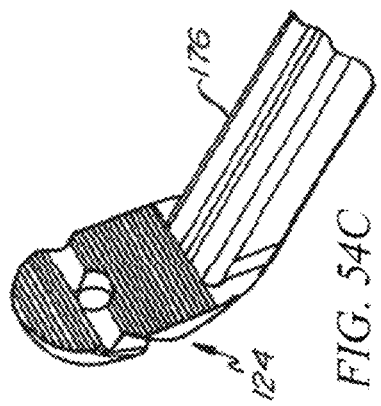

MINIMALLY INVASIVE REPAIR OF A VALVE LEAFLET IN A BEATING HEART

RELATED APPLICATIONS

This application is a continuation of U.S. application Ser. No. 17/892,842 filed Aug. 22, 2022, which is a continuation of U.S. application Ser. No. 16/678,571 filed Nov. 8, 2019, now U.S. Pat. No. 11,419,602, which is a continuation of U.S. application Ser. No. 14/310,807 filed Jun. 20, 2014, now U.S. Pat. No. 10,507,018, which is a continuation of U.S. application Ser. No. 12/254,807 filed Oct. 20, 2008, now U.S. Pat. No. 8,758,393, which claims the benefit of U.S. Provisional Application No. 60/999,431, filed Oct. 18, 2007, U.S. Provisional Application No. 60/999,635, filed Oct. 19, 2007, and U.S. Provisional Application No. 60/999,873, filed Oct. 22, 2007, which are incorporated herein in their entirety by reference.

FIELD OF THE INVENTION

The present invention relates to minimally invasive delivery of a suture. More particularly, the present invention relates to attaching artificial chordae tendineae to a flailing or prolapsing leaflet in a beating heart.

BACKGROUND OF THE INVENTION

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced by excising the valve leaflets of the natural valve and securing a replacement valve in the valve position, usually by suturing the replacement valve to the natural valve annulus. Various types of replacement valves are in current use, including mechanical and biological prostheses, homografts, and allografts.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into a position accessible through the sternotomy. An opening, or atriotomy, is then made in the left atrium, anterior to the right pulmonary veins. The atriotomy is retracted by means of sutures or a retraction device, exposing the mitral valve directly posterior to the atriotomy. One of the aforementioned techniques may then be used to repair or replace the valve.

An alternative technique for mitral valve access may be used when a median sternotomy and/or rotational manipulation of the heart are/is undesirable. In this technique, a large incision is made in the right lateral side of the chest, usually in the region of the fifth intercostal space. One or more ribs may be removed from the patient, and other ribs near the incision are retracted outward to create a large opening onto the thoracic cavity. The left atrium is then exposed on the posterior side of the heat, and an atriotomy is formed in the wall of the left atrium, through which the mitral valve may be accessed for repair or replacement.

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae result in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle. This operation is generally carried out through a median sternotomy and requires cardiopulmonary bypass with aortic cross-clamp and cardioplegic arrest of the heart.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

One alternative to open heart surgery is a robotically guided, thoracoscopically assisted cardiotomy procedure marketed under the tradename of the Da Vinci® system. Instead of requiring a sternotomy, the DaVinci® system uses a minimally invasive approach guided by camera visualization and robotic techniques. Unfortunately, the DaVinci® system is not approved for mitral valve repair procedures on a beating heart. Thus, the use of the DaVinci® system for mitral valve repair still requires a cardiopulmonary bypass with aortic cross-clamp and cardioplegic arrest of the heart.

While there are other laparoscopic and minimally invasive surgical techniques and tools that have been developed, none of these devices are useable for the unique requirements of mitral valve repair on a beating heart. Suturing devices like the Superstich™ vascular suturing device or the Gore® suture passer are designed to permit manual placement of sutures as part of a surgical procedure, but are not designed for use on a beating heart. While certain annuloplasty techniques and instruments that can suture an annuloplasty ring as part of vascular repair or heart bypass surgery may be used in conjunction with a beating heart, these annuloplasty procedures do not involve the capture or retention of a constantly moving leaflet. Consequently, the design and use of annuloplasty techniques and instruments are of little help in solving the problems of developing instruments and techniques for minimally invasive thoracoscopic repair of heart valves.

Recently, a technique has been developed for minimally invasive thoracoscopic repair of heart valves while the heart is still beating. Int'l Pub. No. WO 2006/078694 A2 to Speziali discloses a thoracoscopic heart valve repair method and apparatus. Instead of requiring open heart surgery on a stopped heart, the thorascopic heart valve repair methods and apparatus taught by Speziali utilize fiber optic technology in conjunction with transesophageal echocardiography (TEE) as a visualization technique during a minimally invasive surgical procedure that can be utilized on a beating heart. U.S. Publication No. 2008/0228223 to Alkhatib also discloses a similar apparatus for attaching a prosthetic tether between a leaflet of a patient's heart valve and another portion of the patient's heart to help prevent prolapse of the leaflet and/or to otherwise improve leaflet function.

While the Speziali invention represents a significant advance over open heart techniques for heart valve repair, it would be advantageous to further improve upon this new technique.

SUMMARY OF THE INVENTION

Embodiments of the present invention are generally directed to apparatus and methods for minimally invasive surgical procedures. Although embodiments of the present invention disclosed herein may be adapted or used for any number of purposes, the present invention can generally be used to repair mitral valve leaflets by delivering an implanting one or more sutures to function as artificial chordae tenindae.

In an embodiment, a device for repairing a valve leaflet in a beating heart of a patient comprises a handle assembly, a capture assembly, and a needle head. The handle assembly includes a shaft extending from a distal end of the handle adapted to be extended into a chest cavity of the patient and an actuator mechanism positioned proximate a proximal end of the handle assembly. The shaft has a diameter and a generally circular cross-section along a longitudinal axis at a distal portion of the shaft that is adapted to pass through an incision in the beating heart. The capture assembly extends from the distal portion of the shaft and is adapted to be positioned within the beating heart. The capture assembly has a distal portion including a clamping mechanism adapted to grasp and release the valve leaflet and a proximal portion operably connected to the shaft. The distal portion of the capture assembly has a maximum diameter of an asymmetric cross section transverse to the longitudinal axis of the capture assembly that is greater than the diameter of the shaft. One of a first clamping jaw or a second clamping jaw of the clamping mechanism is selectively positionable along a longitudinal axis of the capture assembly in response to actuation of the actuator mechanism to create a space between interior surfaces of the first clamping jaw and the second clamping jaw having an asymmetric perimeter. The needle head is slidably positionable within the capture assembly to engage a suture at least partially carried by the capture assembly in response to selective activation of a needle by the actuator mechanism as the needle penetrates the valve leaflet. The area of the interior surfaces is increased relative to an interior surface area of a circular clamping jaw having a diameter equal to the diameter of the shaft. The capture assembly is rotatable within the heart with reduced blood loss relative to blood loss of rotation of the asymmetric perimeter of the first clamping jaw and the second clamping jaw in the incision of the heart.

In further embodiments the first clamping jaw and the second clamping jaw may be separable along a bifurcation plane. The bifurcation plane may form a bifurcation angle with the longitudinal axis of the capture assembly. The bifurcation angle may be between approximately forty-five degrees and ninety degrees, or between approximately fifty-five degrees and approximately sixty-five degrees. The area of the interior surfaces may be increased relative to the interior surface area of a circular clamping jaw having a diameter equal to the diameter of the shaft by between 20% and 100%, or between 30% and 50%. The diameter of the shaft may be less than 12 mm, or less than 9 mm. The space between interior surfaces of the first clamping jaw and the second clamping jaw of the distal tip portion, when positioned in an open position, may provides a distance along the longitudinal axis of the capture assembly between interior surfaces of the first clamping jaw and the second clamping jaw of between 1 and 5 cm, or between 2 and 3 cm. The capture assembly may be configured to penetrate the valve leaflet with the needle head from a distance of between approximately one millimeter and approximately four millimeters from a leading edge of the valve leaflet. The distal portion of the shaft may be isodiametric and the proximal portion of the capture assembly may include a tapered region having cross sections that transition from a substantially circular cross section of the distal portion of the shaft to the asymmetric perimeter of the first clamping jaw and the second clamping jaw. The distal portion of the capture assembly may have a generally oblong asymmetric egg three dimensional shape, with the bifurcation angle being approximately 60 degrees and the asymmetric perimeter of the first clamping jaw and the second clamping jaw being generally loaf shaped cross section.

In an embodiment, a device for repairing a valve leaflet in a beating heart of a patient comprises a shaft, a handle, a capture assembly, and a needle. The shaft has a proximal end outside the patient and a distal end adapted for insertion into the beating heart of the patient. The handle has an actuator operably connected to the proximal end of the shaft. The capture assembly is adapted to penetrate the beating heart, operably coupled to the distal end of the shaft, and includes a clamping mechanism, bifurcated tip, adapted to grasp the valve leaflet in response to selective actuation of the actuator. The needle is slidably positionable within the capture assembly to penetrate the valve leaflet. The shaft is generally isodiametric. The capture assembly has a cross-sectional perimeter that is asymmetric at the bifurcated tip. A maximum diameter of the cross sectional perimeter at the bifurcated tip is greater than a diameter of a portion of the shaft adapted to be positioned proximate a wall of the beating heart.

In further embodiments, the handle may include a first actuator extending generally outwardly the handle for lateral operation and a second actuator generally axially along the handle for inline operation. The first actuator may be operably connected to the needle assembly and the second actuator may be operably connected to the capture assembly. The handle may define a first and second spaced-apart aperture and the actuator may define a third aperture. The first, second, and third apertures may be adapted to receive fingers of an operator. The handle and the actuator may also be adapted for robotic control. The robotic control may be performed by a multi-axis control system. The capture assembly may include a pivot joint operably controllable by the multi-axis control system. The capture assembly may be pivotable about at least two axes of rotation.

In an embodiment, device for repairing a valve leaflet in a beating heart of a patient comprises a handle assembly, a capture assembly, a needle head, and a capture confirmation system. The handle assembly includes a shaft extending from a distal end of the handle adapted to be extended into a chest cavity of the patient and an actuator mechanism positioned proximate a proximal end of the handle assembly. The capture assembly extends from the distal portion of the shaft and is adapted to be positioned within the beating heart. The capture assembly has a distal portion including a clamping mechanism adapted to grasp and release the valve leaflet. The capture assembly also has a proximal portion operably connected to the shaft. A first clamping jaw of the clamping mechanism is selectively positionable along a longitudinal axis of the capture assembly in response to actuation of the actuator mechanism to create a space between interior surfaces of the first clamping jaw and a second clamping jaw. The clamping mechanism has an asymmetric perimeter. The capture assembly further includes a plurality of pairs of fiber optic fibers. Each pair of fibers has a transmission fiber and a return fiber terminated on a distal end at an interior surface of the clamping mechanism where the fiber extends through the shaft and out of the handle assembly to a proximal end beyond the handle assembly. The needle head is slidably positionable within the capture assembly to engage a suture at least partially carried by the capture assembly in response to selective activation of a needle by the actuator mechanism as the needle penetrates the valve leaflet. The capture confirmation system verifies capture of the valve leaflet in the space between the interior surfaces of the first clamping jaw and the second clamping jaw. The capture confirmation system includes a housing separate from the handle assembly and at least one lense. The housing separate from the handle assembly contains a battery powered optical light source in optical communication with a proximal end of each transmission fiber. The at least one lens is visible from an exterior surface of the housing and in optical communication with a proximal end of each return fiber to display light received from the space between the interior surfaces of the first clamping jaw and the second clamping jaw corresponding to the distal end of each return fiber as an indication of whether there is capture of the valve leaflet by the capture assembly.

In further embodiments, the capture confirmation system may provide a binary indication of whether the valve leaflet is grasped between the interior surfaces of the first clamping jaw and the second clamping jaw by displaying a first color when a surface of the valve leaflet confronts the fiber optic pairs at the interior surfaces and a second color when the valve leaflet does not confront the fiber optic pairs at the interior surfaces. The first color may be indicative of blood and the second color is indicative of valve leaflet. The optical light source may be a light-emitting diode (LED) and the proximal end of the transmission fiber may be positioned less than approximately 0.5 cm from the LED, or between approximately 0.1 cm and approximately 0.2 cm from the LED. Each lens may have a thickness of between approximately 0.2 cm and approximately 0.5 cm, or between approximately 0.3 cm and approximately 0.35 cm. The proximal end of each return fiber may be positioned within approximately 0.3 cm of the corresponding lens, or between approximately 0.15 cm and approximately 2 cm of the corresponding lens. The shaft may define a needle lumen adapted to receive the needle and the pairs of fiber optic fibers may be carried by the shaft outside the needle lumen. Each pair of fiber optic fibers may include at least approximately 1 m of length external to the handle such that the housing of the capture confirmation system is positionable proximal a separate patient display apparatus after insertion of the device into the chest cavity of the patient.

In an embodiment, a device for repairing a valve leaflet in a beating heart of a patient comprises a handles assembly, a capture assembly, and a needle head. The handle assembly includes a shaft extending from a distal end of the handle and is adapted to be extended into a chest cavity of the patient. The shaft includes a first channel adapted to receive a suture and a second channel adapted to receive a needle. The handle assembly also includes an actuator mechanism and a suture retention mechanism. The capture assembly extends from a distal portion of the shaft and is adapted to be positioned within the beating heart. The capture assembly has a distal portion including a clamping mechanism adapted to grasp and release the valve leaflet and a proximal portion operably connected to the shaft. The needle head is slidably positionable within the capture assembly to engage the suture at least partially carried by the capture assembly in response to selective activation of the needle by the actuator mechanism as the needle penetrates the valve leaflet. The suture retention mechanism selectively tensions the suture across a path of travel of the needle through the needle head prior to engagement by the needle.

In further embodiments, the capture assembly may define a needle detent and the suture may be substantially taught across the needle detent. The needle head may present a hook adapted to receive the suture.

In an embodiment, a device for repairing a valve leaflet in a beating heart of a patient may comprise a handle assembly, a capture assembly, and a needle head. The handle assembly includes a shaft and an actuator mechanism. The shaft extends from a distal end of the handle and is adapted to be extended into a chest cavity of the patient. The actuator mechanism is positioned proximate a proximal end of the handle assembly. The capture assembly extends from the distal portion of the shaft and is adapted to be positioned within the beating heart. The capture assembly has a distal portion and a proximal portion. The distal portion includes a clamping mechanism adapted to grasp and release the valve leaflet. The proximal portion is operably connected to the shaft. A first clamping jaw of the clamping mechanism is selectively positionable along a longitudinal axis of the capture assembly in response to actuation of the actuator mechanism to create a space between interior surfaces of the first clamping jaw and a second clamping jaw. The needle head is slidably positionable within the capture assembly to engage a suture at least partially carried by the capture assembly in response to selective activation of a needle by the actuator mechanism as the needle penetrates the valve leaflet. At least one of the handle assembly or the capture assembly includes a biasing member adapted to bias at least one of the first clamping jaw and the second clamping jaw with respect to one another such that selective actuation of the actuator mechanism overcomes the biasing member before the space is created or closed between the interior surfaces of the first clamping jaw and the second clamping jaw.

In further embodiments, the first clamping jaw and the second clamping jaw may be biased toward a closed position. The biasing member may exert a force of between approximately one pound per square-inch and approximately ten pounds per square-inch, or approximately five pounds per square-inch.

In an embodiment, a method of repairing a valve leaflet in a beating heart of a patient includes using any of the embodiments of the devices described heretofore.

In an embodiment, a method of providing instruments and instructions for repairing a valve leaflet comprises any of the embodiments of the described heretofore and providing instructions for operating any of the embodiments described heretofore to repair the valve leaflet.

In further embodiments, the device can be used in conjunction with external transesophageal echocardiography (TEE) to visualize a valve leaflet to verify leaflet capture. In various embodiments, the device can provide assistance in performing repair of heart valves through a midline sternotomy during cardiopulmonary by-pass thoracotomy modalities, including anterolateral thoracotomy, in addition to minimally invasive procedures.

Throughout the specification, any references to such relative terms as top and bottom, and the like are intended for convenience of description and are not intended to limit the present invention or its components to any one positional or spatial orientation. It will be further understood that various dimensions of the components in the attached figures may vary depending upon specific applications and intended use of the invention without departing from the scope of the invention.

BRIEF DESCRIPTION OF THE DRAWINGS

The embodiments of the present invention may be more completely understood in consideration of the following detailed description of various embodiments in connection with the accompanying drawings, in which:

FIG. 1A is a perspective view of a device for delivering and manipulating a suture in a beating heart, according to an embodiment of the present invention;

FIG. 1B is a perspective view of a device for delivering and manipulating a suture in a beating heart, according to an embodiment of the present invention;

FIG. 2 is a front/top perspective view of the handheld suture deployment device depicted in FIG. 1A;

FIG. 3 is a front/top perspective view of the handheld suture deployment device depicted in FIG. 1A;

FIG. 4D is a rear/side perspective view of the open distal tip of the handheld suture deployment device depicted in FIG. 2;

FIG. 4E is a front/side perspective view of the open distal tip of the handheld suture deployment device depicted in FIG. 2;

FIG. 4F is a front/bottom perspective view of the upper clamp jaw and shaft of the handheld suture deployment device depicted in FIG. 2;

FIG. 4G is a front/side perspective view of the open distal tip of the handheld suture deployment device depicted in FIG. 2;

FIG. 4H is a side elevation view of the open distal tip of the handheld suture deployment device depicted in FIG. 2;

FIG. 4I is a rear/top perspective view of the open distal tip of the handheld suture deployment device depicted in FIG. 2;

FIG. 4J is a rear/top perspective view of the open distal tip of the handheld suture deployment device depicted in FIG. 2;

FIG. 5 is a front/top perspective view of the pre-loaded suture cartridge depicted in FIG. 2;

FIG. 5B (view B) is a front/top perspective view of the proximal end of a pre-loaded suture cartridge;

FIG. 5E (view B, cartridge in phantom) is a front/top perspective view of the proximal end of a pre-loaded suture cartridge;

FIG. 6 is a front/top perspective view of the operating room loaded cartridge depicted in FIG. 3;

FIG. 6A (rotated) is a rear/top perspective view of the distal end of a operating room loaded cartridge;

FIG. 7 is a front/top perspective view of the needle assembly depicted in FIG. 1A;

FIG. 7A is a front/top perspective view of the distal end of a needle assembly;

FIG. 8 is a rear/top perspective view of an extended needle within the open distal tip of the handheld suture deployment device depicted in FIG. 1A;

FIG. 8A is a front/top perspective view of the proximal end of the handheld suture deployment device depicted in FIG. 1A with the needle assembly in the start position;

FIG. 8B is a front/top perspective view of the proximal end of the handheld suture deployment device depicted in FIG. 1A with the needle assembly in the start position;

FIG. 8C is a front/top perspective view of the proximal end of the handheld suture deployment device depicted in FIG. 1A with the needle assembly in the fully advanced position;

FIG. 8D is a front/top perspective view of the proximal end of the handheld suture deployment device depicted in FIG. 1A with a retracted needle assembly;

FIG. 10 is a rear/bottom perspective view of the proximal end of the handheld suture deployment device depicted in FIG. 1A;

FIG. 11 is a front/top perspective view of the plunger assembly depicted in FIG. 8A;

FIG. 12 is a front/top perspective view depicting fiber optic cable assembly depicted in FIG. 1A and leaflet capture verification monitor depicted in FIG. 1A;

FIG. 26 is a side/bottom perspective view of a mitral valve leaflet in need of repair captured by the clamp of the handheld suture deployment device depicted in FIG. 1A, with the clamp shown in phantom;

FIG. 27 is a side/bottom perspective view of a mitral valve leaflet in need of repair captured by the clamp of the handheld suture deployment device depicted in FIG. 1A, with the clamp shown in phantom;

FIG. 28 is a top/rear perspective view of the handheld suture deployment device depicted in FIG. 1A;

FIG. 29 is a top/rear perspective view of the handheld suture deployment device depicted in FIG. 1A;

FIG. 50 is a top/rear perspective view of the open distal tip of the handheld suture deployment device depicted in FIG. 2;

FIG. 51 is a top/front perspective view of the open distal tip of the handheld suture deployment device depicted in FIG. 2;

FIG. 52 is a top plan view of the open distal tip of the handheld suture deployment device depicted in FIG. 2;

FIG. 53 is a front perspective view of the open distal tip of the handheld suture deployment device depicted in FIG. 2.

FIG. 54A-C is a top plan view and a side elevation view of the suture cartridge depicted in FIG. 1A; and FIG. 55 is a side elevation view and a front/bottom perspective view of the shaft depicted in FIG. 1A.

Figure 4A:
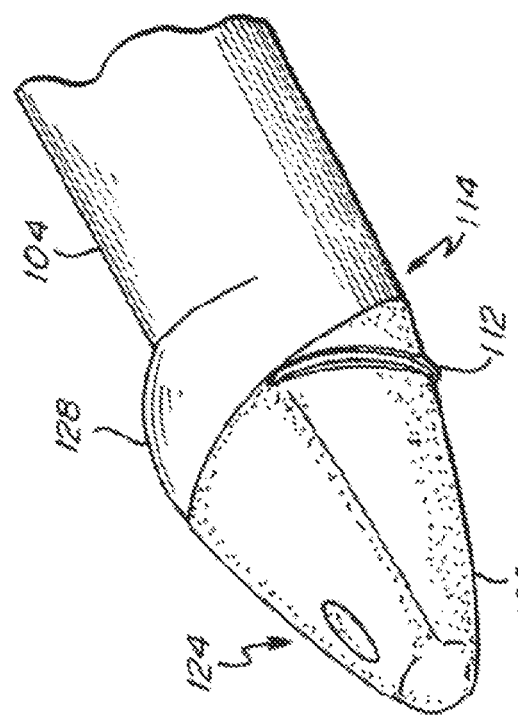
FIG. 4A is a front/top perspective view of the distal tip of the handheld suture deployment device depicted in FIG. 1A.
Figure 4B:
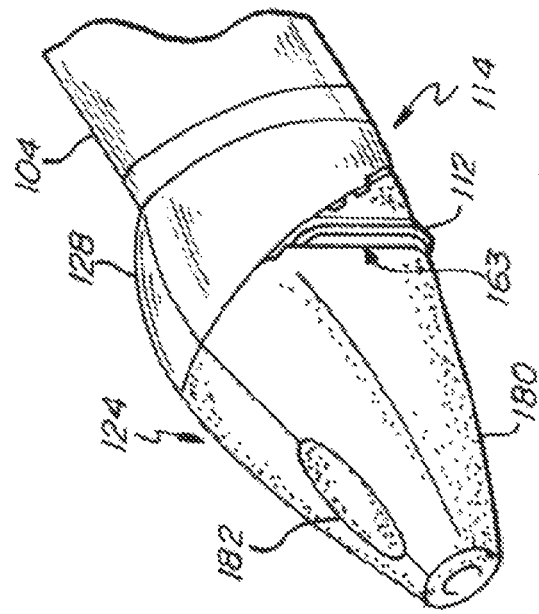
FIG. 4B is a front/top perspective view of the distal tip of the handheld suture deployment device depicted in FIG. 2.
Figure 4C:
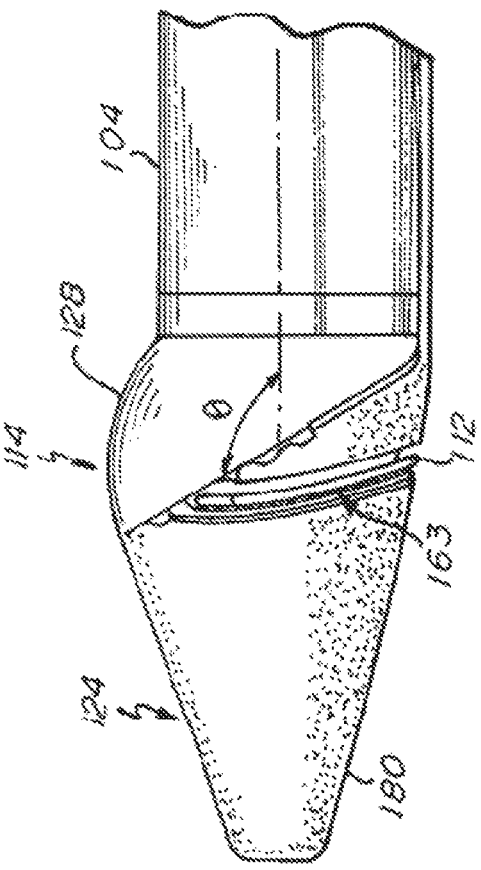
FIG. 4C is a side elevation view of the distal tip of the handheld suture deployment device depicted in FIG. 2.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE DRAWINGS

Certain embodiments of the present invention are directed to apparatus, systems and methods for performing thoracotomy modalities to repair heart valves in either a beating heart or a heart during cardiopulmonary by-pass; or thoracoscopic repair of heart valves in a beating heart. A device that can be used for these purposes is depicted generally with reference numeral 100.

Although the methods and apparatuses of the present invention can be used for any number of treatments requiring the delivery and manipulation of a suture, the present invention, according to certain embodiments, is generally intended for use in treating a heart condition known as mitral valve regurgitation (MR). Mitral valve regurgitation, which is also commonly referred to as mitral insufficiency or mitral incompetence, is a condition characterized by failure of the mitral valve to close properly. When the mitral valve does not close tightly, blood is allowed to flow backward in relation to its normal flow path within the heart. As many as one in five people over fifty-five years of age have some degree of mitral valve regurgitation.

Figures 44, 45A, 45B:
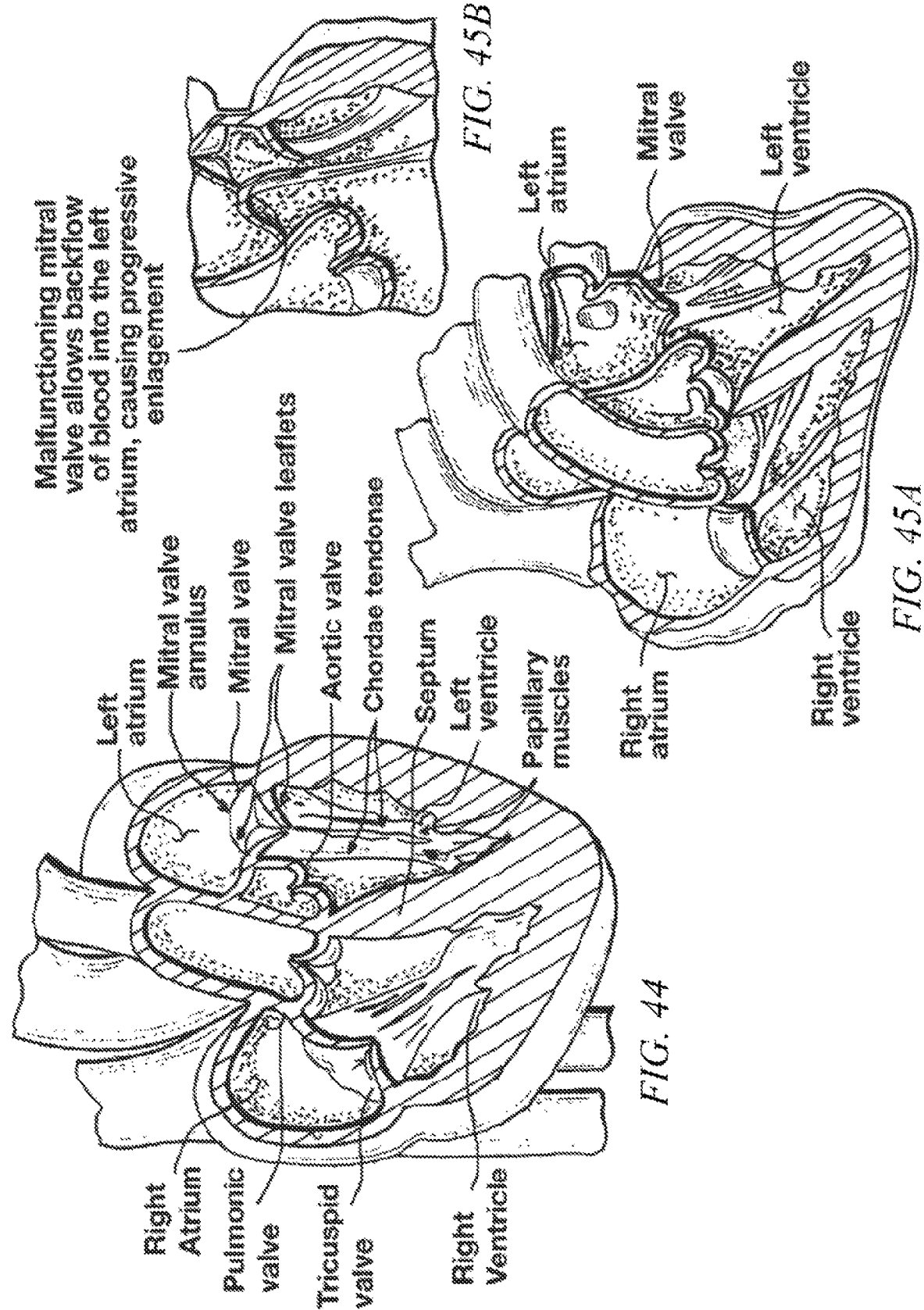
FIG. 44 is a cross-sectional view of a heart.
FIG. 45A is a cross-sectional view of a heart with a normal mitral valve.
FIG. 45B is a partial cross-sectional view of a heart with an abnormal mitral valve.

As depicted in FIGS. 44-45, the heart has four chambers. The two upper chambers, called the left and right atria, receive blood. The two lower chambers, called the left and right ventricles, pump blood. Four valves aid in directing blood flow through the heart's chambers. These heart valves open and close, allowing blood to flow in only one direction.

Figures 42, 43:
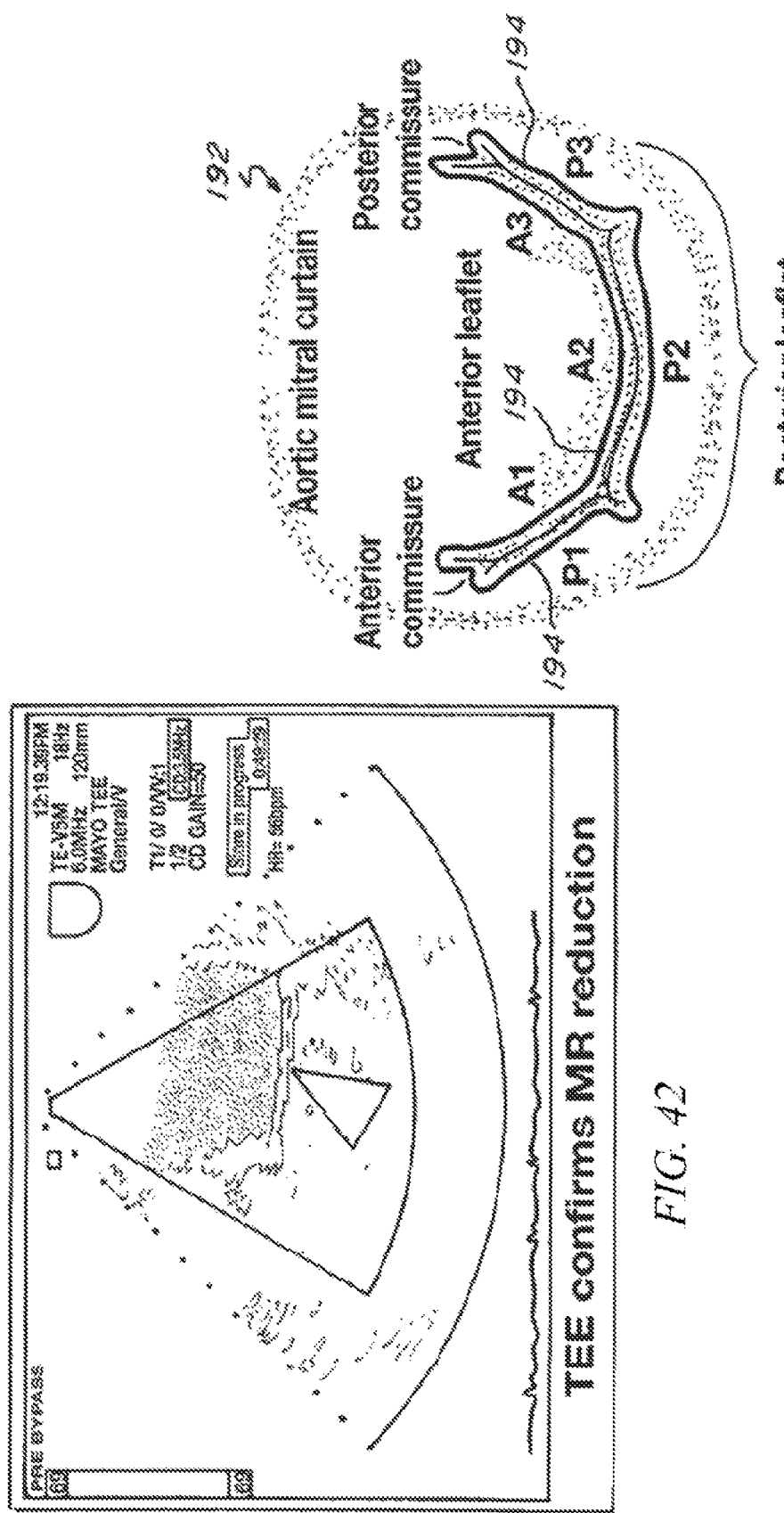
FIG. 42 is screen capture of the display of an external transesophageal echocardiography showing a reduction in MR.
FIG. 43 is a schematic top plan view of a mitral valve.

A mitral valve is depicted illustratively in FIGS. 43-45. Situated between the left atrium and left ventricle, the mitral valve consists of two flaps of tissue, or leaflets. The mitral valve annulus forms a ring around the valve leaflets, thereby connecting the leaflets to the heart muscle. Papillary muscles are located at the base of the left ventricle. Anchoring the mitral valve leaflets to the papillary muscles are tendon-like cords called chordae tendineae. Normal chordae tendineae prevent the leaflets from prolapsing, or inverting, into the left atrium, as depicted in FIG. 45A.

Under normal cardiac conditions, the left atrium contracts and forces blood through the mitral valve and into the left ventricle. As the left ventricle contracts, hemodynamic pressure forces the mitral valve shut and blood is pumped through the aortic valve into the aorta. For the mitral valve to shut properly, the valvular edges of the valve leaflets must form a non-prolapsing seal that prevents the backflow of blood during left ventricular contraction.

A properly functioning mitral valve opens and closes fully. When the mitral valve fails to fully close, as depicted in FIG. 45B, blood from the left ventricle is able to flow backward into the left atrium instead of flowing forward into the aorta. This backflow of blood through the heart valve is called regurgitation. The regurgitation of blood through the heart due to the failure of the mitral valve to close properly is the condition known as mitral valve regurgitation. A common symptom of mitral valve regurgitation is congestion of blood within the lungs.

When blood regurgitates from the left ventricle into the left atrium, such as due to MR, less blood is pumped into the aorta and throughout the body. In an attempt to pump adequate blood to meet the blood needs of the body, the left ventricle tends to increase in size over time to compensate for this reduced blood flow. Ventricular enlargement, in turn, often leads to compromised contractions of the heart, however, thereby exacerbating the congestion of blood within the lungs. If left untreated, severe MR can eventually lead to serious cardiac arrhythmia and/or congestive heart failure (CHF).

Mitral valve regurgitation can be caused by any number of conditions, including mitral valve prolapse (a condition in which the leaflets and chordae tendineae of the mitral valve are weakened resulting in prolapse of the valve leaflets, improper closure of the mitral valve, and the backflow of blood within the heart with each contraction of the left ventricle), damaged chords (wherein the chordae tendineae become stretched or ruptured, causing substantial leakage through the mitral valve), rheumatic fever (the infection can cause the valve leaflets to thicken, limiting the valve's ability to open, or cause scarring of the leaflets, leading to regurgitation), endocarditis (an infection inside the heart), deterioration of the mitral valve with age, prior heart attack (causing damage to the area of the heart muscle that supports the mitral valve), and a variety of congenital heart defects. Normally, mitral valve regurgitation does not pose a serious health threat. As MR becomes exacerbated over time, however, the condition can become more severe, resulting in life-threatening complications, including atrial fibrillation (an irregular heart rhythm in which the atria beat chaotically and rapidly, causing blood clots to develop and break loose and potentially result in a stroke), heart arrhythmias, and congestive heart failure (occurring when the heart becomes unable to pump sufficient blood to meet the body's needs due to the strain on the right side of the heart caused by fluid and pressure build-up in the lungs).

Figure 46:
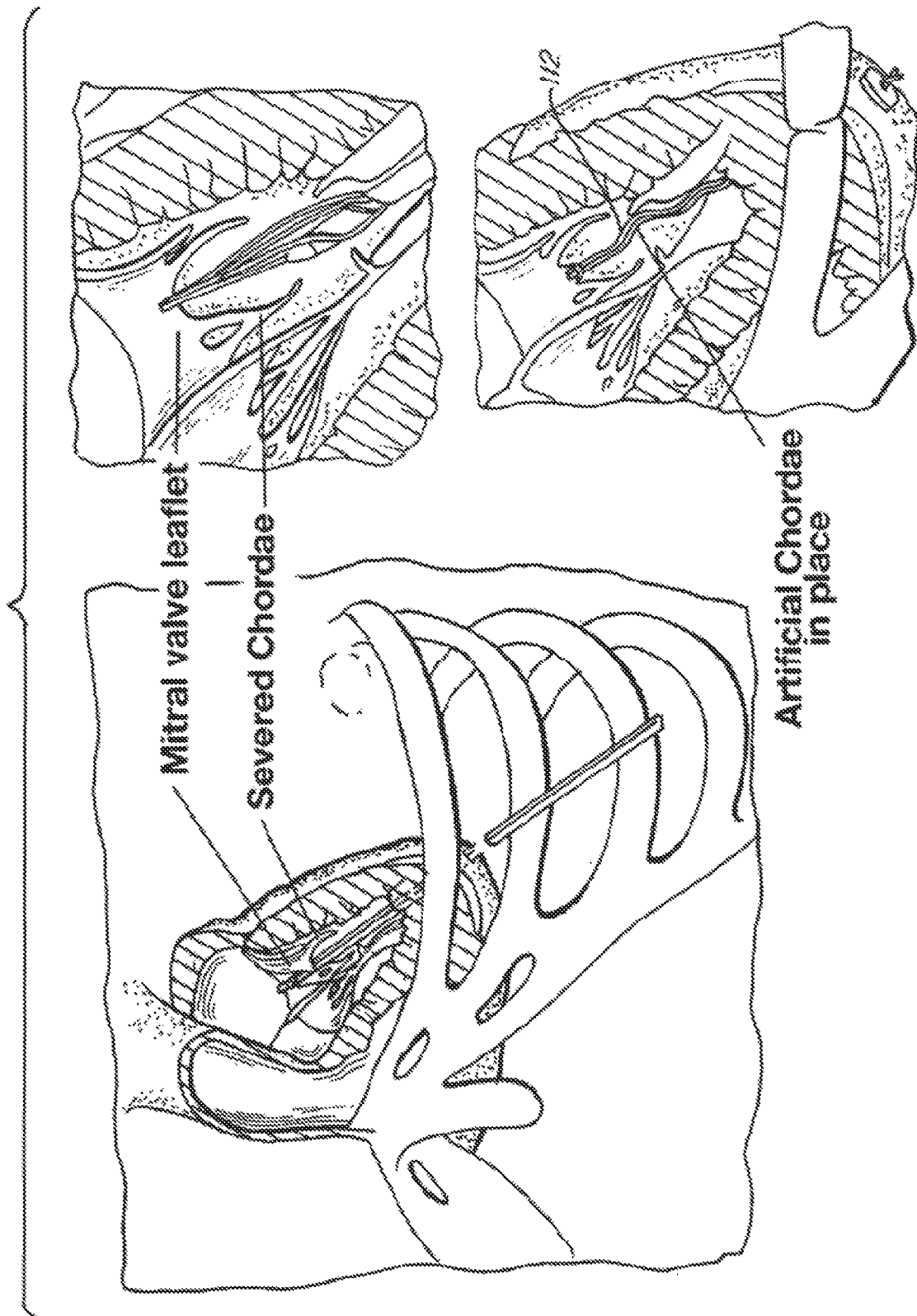
FIG. 46 is an perspective partial cut-away front view of apical access of a heart with insets showing the mitral valve leaflets and chordae tendonae.
Figure 47:
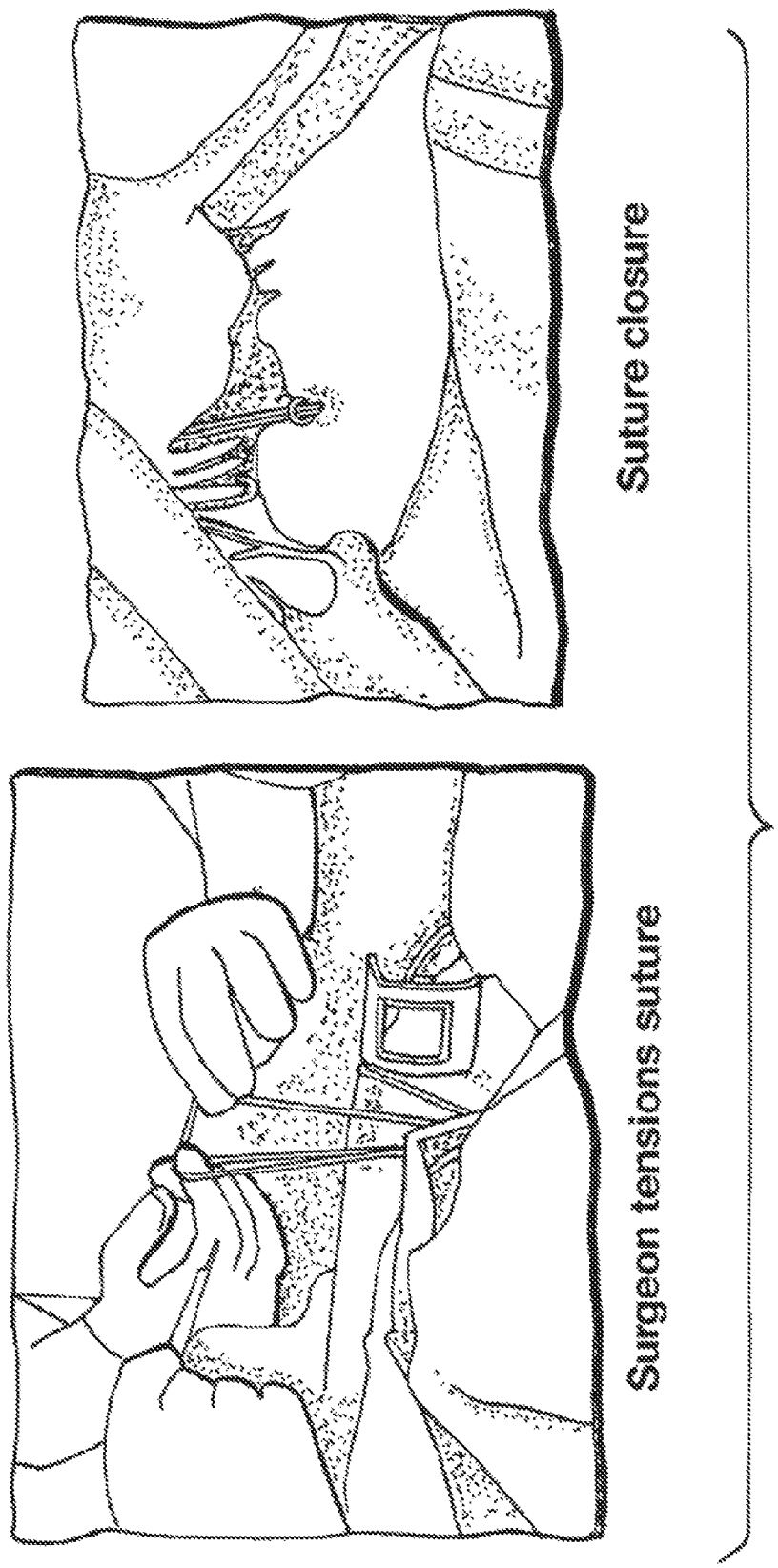
FIG. 47 is a view of a surgeon tensioning a suture and of a suture securing a leaflet.
Figure 48:
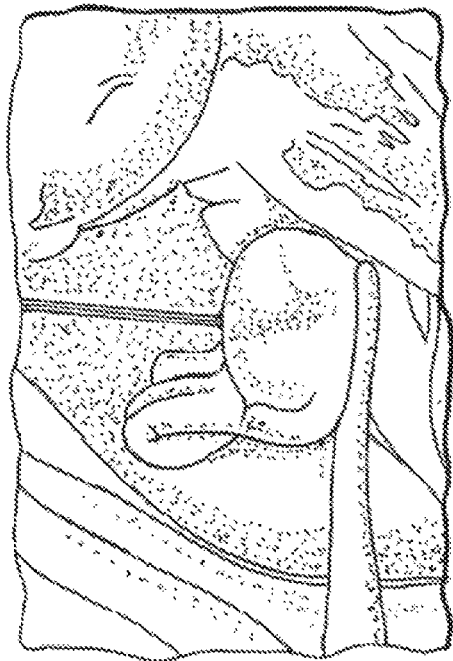
FIG. 48 is a view of a suture securing a leaflet.
Figure 49:
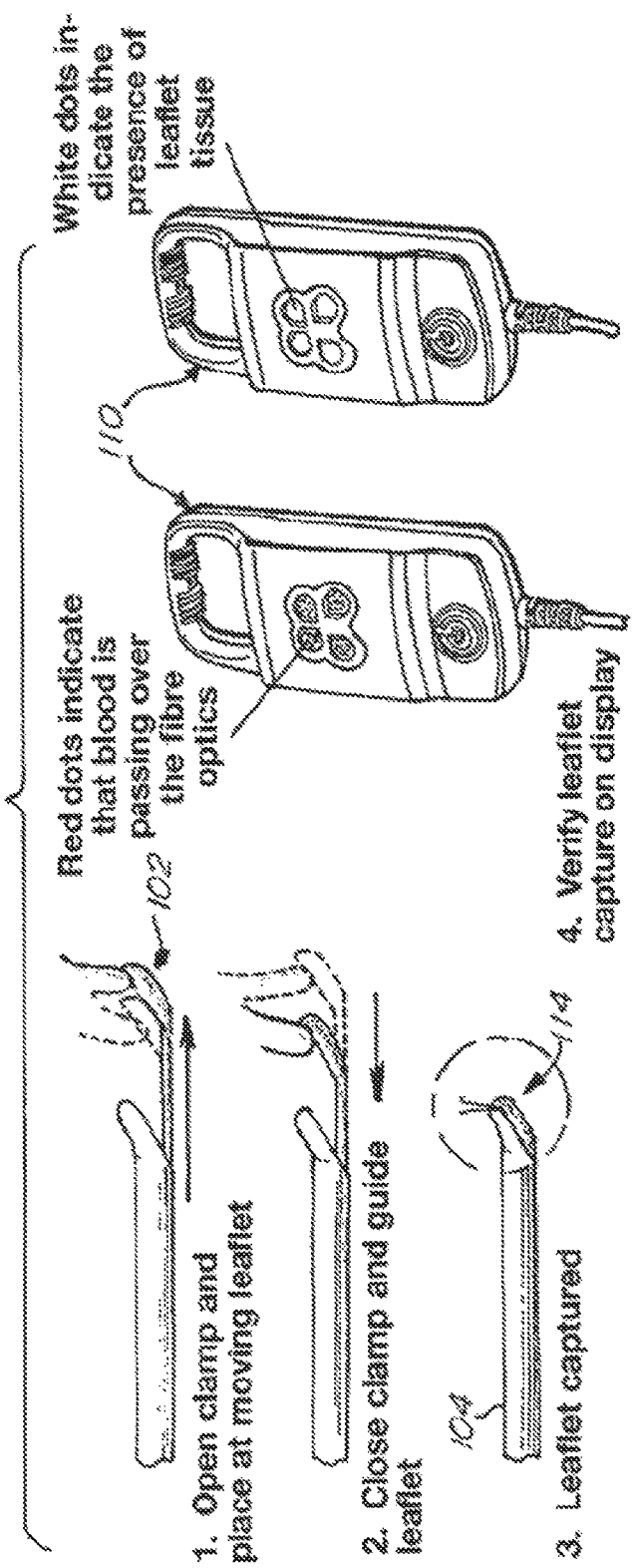
FIG. 49 is a series of side elevation views of the open distal tip of the handheld suture deployment device depicted in FIG. 2 capturing a leaflet, and two front perspective views of the leaflet capture verification monitor depicted in FIG. 1A.

According to certain embodiments, the present invention generally reduces the need to treat mitral valve regurgitation in most individuals with a sternotomy and cardiopulmonary bypass surgery. Specifically, the present invention can provide a minimally invasive treatment of MR. This treatment significantly decreases trauma to surgical patients by facilitating transapical access of a beating heart via a lateral thoracotomy, as depicted in FIG. 46, in a manner that eliminates certain surgical steps normally required to complete mitral valve repair procedure by sternotomy.

Transapical access to a heart includes all entry points that are within approximately the bottom third of the heart. As used in this patent application, transapical access to a heart includes all directions of entry and points of entry, as well as all angles of entry at each entry point.

According to certain embodiments, the present invention is compatible with, and directed to percutaneous access to the heart. According to other embodiments, the present invention is compatible with, and directed to other access points to a heart.

Referring to FIG. 1B, device 100 may include handle assembly 300, capture assembly 302, and needle 138 according to an embodiment of the present invention. Handle assembly 300 generally has distal end 304 and proximal end 306. Handle assembly includes shaft 308 and actuator 309. Shaft 308 extends from distal end 304 of handle assembly 300 and is generally adapted to be extended into the chest cavity of a patient. Actuator 309 is positioned proximate proximal end 306. Capture assembly 302 generally has distal portion 310 and proximal portion 312. Distal portion 310 includes clamping mechanism 314 formed by first clamping jaw 316 and second clamping jaw 318. In an embodiment, clamping mechanism 314 is adapted to grasp and release a valve leaflet. In a further embodiment, first clamping jaw 316 or second clamping jaw 318 is selectively positionable along a longitudinal axis of capture assembly 302 in response to actuation of actuator mechanism 314 to create a space between the interior surfaces (not shown) of the first and second clamping jaws 316, 318.

Referring to FIG. 1A, device 100 can deliver and manipulate a suture in a beating heart and generally includes a handheld suture deployment device 118, and capture confirmation system 101, according to an embodiment of the invention. The handheld suture deployment device 118 generally includes a suture cartridge 102, a shaft 104, a handle 106, and a needle assembly 116. Capture confirmation system 101 generally includes fiber optic cable assembly 108, and leaflet capture verification (LCV) monitor 110. Although device 100 can be used for any number of purposes without departing from the spirit or scope of the present invention, the aforementioned platform of components, as is described hereinafter in further detail, enable the extending of a shaft through the chest cavity and into a beating heart chamber to capture a valve leaflet of a valve needing repair, and to further provide a needle to operably penetrate the captured valve leaflet and draw a suture therethrough Suture cartridge 102 may be pre-loaded suture cartridge 120 or operating room-loaded cartridges 122. Referring to FIG. 5, pre-loaded suture cartridge 120 can include a tapered lower clamp jaw 124, a suture 112, a suture retention system 130, a handle interface 174, a channel 131, and a groove on the clamp surface 162a. Suture cartridge 120 has proximal 198 and distal 196 ends. The lower clamp jaw 124 is located at the distal end 196 of suture cartridge 120. The handle interface 174 is located at the proximal end 198 of suture cartridge 120. Channel 131 is provided with a pair of openings, a first opening which is located on the top surface, and a second opening which is located on the bottom surface of suture cartridge 120. Channel 131 runs vertically through suture cartridge 120, and is located near the proximal end 198 of suture cartridge 120, such that channel 131 and handle interface 174 are located generally adjacent to one another. Intermediate channel 131 and lower clamp jaw 124 is a cartridge shaft 176.

Referring to FIGS. 4A-4E, 4G-4J and FIG. 5, lower clamp jaw, or distal tip portion, 124 is provided on the distal end of suture cartridge 120 according to an embodiment of the invention. For example, lower clamp jaw 124 and upper clamp jaw 128 may work cooperatively to form a low profile, tapered tip grasping device. Lower clamp jaw 124 generally includes a low profile tip 180, a lumen 182, a groove 162, a lower clamp surface 126 and two channels 163. Lumen 182 extends from the distal end to the proximal end of lower clamp jaw 124, parallel to the axis of cartridge shaft 176. Lumen 182 can be substantially straight, with an inner diameter adapted to receive needle end 146. Groove 162 can be either groove 162a or groove 162b.

According to an embodiment of this invention, groove 162a is disposed on lower clamp surface 126, and is located laterally along surface 126, as depicted in FIG. 4D. The depth and width of groove 162a is generally equal to, or greater than, the diameter of suture 112.

According to an embodiment, groove 162b is disposed on the upper surface of lower clamp surface 126, as depicted in FIGS. 4G-4J. The depth and width of groove 162b is generally equal to, or greater than, the diameter of suture 112. For embodiment of this invention where groove 162 is groove 162b, cutout 161 is provided, as depicted in FIGS. 4G, 4I, and 4J. Cutout 161 is generally a groove that is parallel with, and has a width that is generally at least equal to the diameter of lumen 182. The distal end of cutout 161 joins with groove 162b and the proximal end extends to surface 126. The depth of cutout 161 extends from the surface of lower clamp jaw 124 to the centerline of lumen 182.

According to an embodiment, a lower clamp surface 126 is defined by the generally planar canted surface of lower clamp jaw 124. Clamping plane 129 is the planar distal face of upper clamp jaw 128. Clamp 114 is in a closed position when lower clamp surface 126 contacts clamping plane 129. Lower clamp surface 126 has a surface finish generally suitable for retaining a grasped valve leaflet. Suitable surface finishes include a striated or textured surface finish. As depicted in FIGS. 4D, 4I-4J, and 5, a suitable surface finish may include a series of groves and ridges.

According to an embodiment, the proximal opening of lumen 182 is located to intersect groove 162a, as depicted in FIG. 4D and view A of FIG. 5. According to another embodiment, the proximal opening of lumen 182 is located to intersect groove 162b, as depicted in FIGS. 4I and 4J.

According to an embodiment, the low profile tip 180 is generally smooth in shape and surface finish, and is generally free of sharp edges or points. The low profile tip 180 is sufficiently large so that when needle assembly 116 is in a fully extended position, needle end 146 does not protrude from the distal opening of lumen 182.

According to an embodiment, cartridge shaft 176 is provided with a cross-sectional profile that is compatible to be slidably retained within cartridge channel 172. Cartridge shaft 176 is relatively wide, in comparison to the diameter of shaft 104, as depicted in FIGS. 50-53. In an embodiment, the width of cartridge shaft 176 is approximately 65% of the diameter of shaft 104. In another embodiment, the width of cartridge shaft 176 is between approximately 65% and approximately 100% of the diameter of shaft 104. In another embodiment, the width of cartridge shaft 176 is less than approximately 65% of the diameter of shaft 104. A wide cartridge shaft 176 can prevent body tissue from entering clamp 114 from the bottom and presenting a false capture by capture confirmation system 101.

According to an embodiment, groove 178 is longitudinally disposed along the centerline of the top surface of shaft 176. The depth of groove 178 is generally equal to, or greater than, the diameter of suture 112. The cross-sectional area is generally sufficient to simultaneously encompass the cross-sectional area of two sutures 112.

Figure 5A:
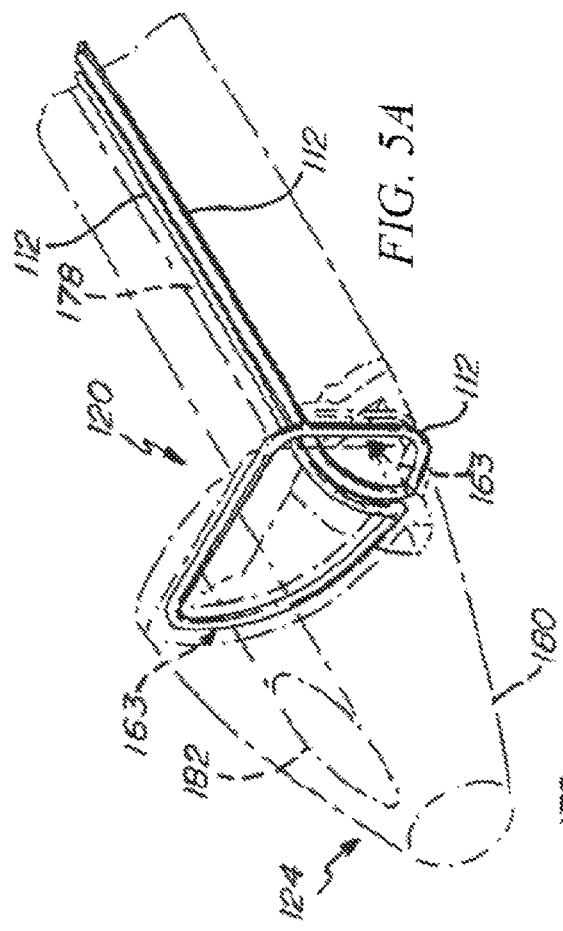
FIG. 5A (view A cartridge in phantom) is a front/top perspective view of the distal end of a pre-loaded suture cartridge.
Figure 5C:
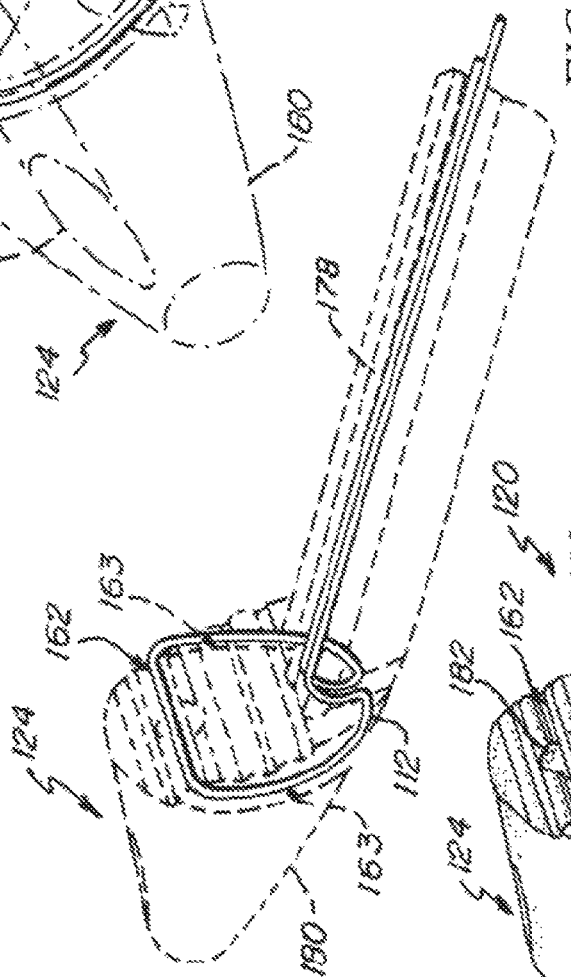
FIG. 5C (view A, rotated, cartridge in phantom) is a rear/top perspective view of the distal end of a pre-loaded suture cartridge.
Figure 5D:
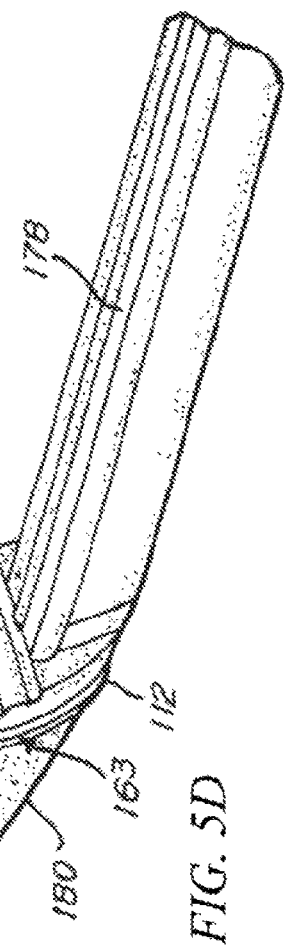
FIG. 5D (view A, rotated) is a rear/top perspective view of the distal end of a pre-loaded suture cartridge.

According to certain embodiments of this invention, channels 163 are provided along a portion of the proximal surface of lower clamp jaw 124, as depicted in FIG. 5A. The depth of channels 163 is generally equal to, or greater than, the diameter of suture 112. As depicted in FIG. 5A (view A cartridge in phantom), channels 163 also form a combined cavity that extends generally from the bottom surface of lower clamp jaw 124 to the distal top surface of cartridge shaft 176. The proximal ends of channels 163 open to groove 178, and the proximal end of groove 178 opens to channel 131, thus providing a continuous path for suture 112.

According to an embodiment of this invention, suture 112 is fed through the suture cartridge 120, as depicted in FIG. 5. The length of suture 112 is generally divided into two halves, with the mid-point of the suture length generally located within groove 162*a*. Suture 112 runs along the entire length of groove 162*a* and channels 163. Suture 112 is also located within groove 178 and channel 131. The two free ends of suture 112 extend through channel 131.

The suture retention system 130 may generally include a J-shaped flat spring located near the proximal end of suture cartridge 120. The straight portion of the "J" is generally parallel with, and located near, the top surface of suture cartridge 120. The curved portion of the "J" generally descends into channel 131. The suture retention system 130 is positioned such that the curved portion of the "J" forms an interference fit with the distal wall of channel 131. The suture retention system 130 acts to retain suture 112 in place within suture cartridge 102 by applying a frictional force on the portion of suture 112 that passes through channel 131. The frictional force generally acts to retain suture 112 as fed within suture cartridge 102. Suture retention system 130 can release suture 112 once needle 138 has been advanced to a fully extended position, as depicted in FIG. 8C.

According to an embodiment, handle interface 174 is located on the proximal end 198 of suture cartridge 120. Handle interface 174 is provided with suitable structure for being releasably retained within handle 106. Handle interface 174 may also be provided with suitable structure for being releasably retained within plunger assembly 152. Suitable structure may include, for example, latches, screws, friction fit attachments, and the like.

Figure 9:
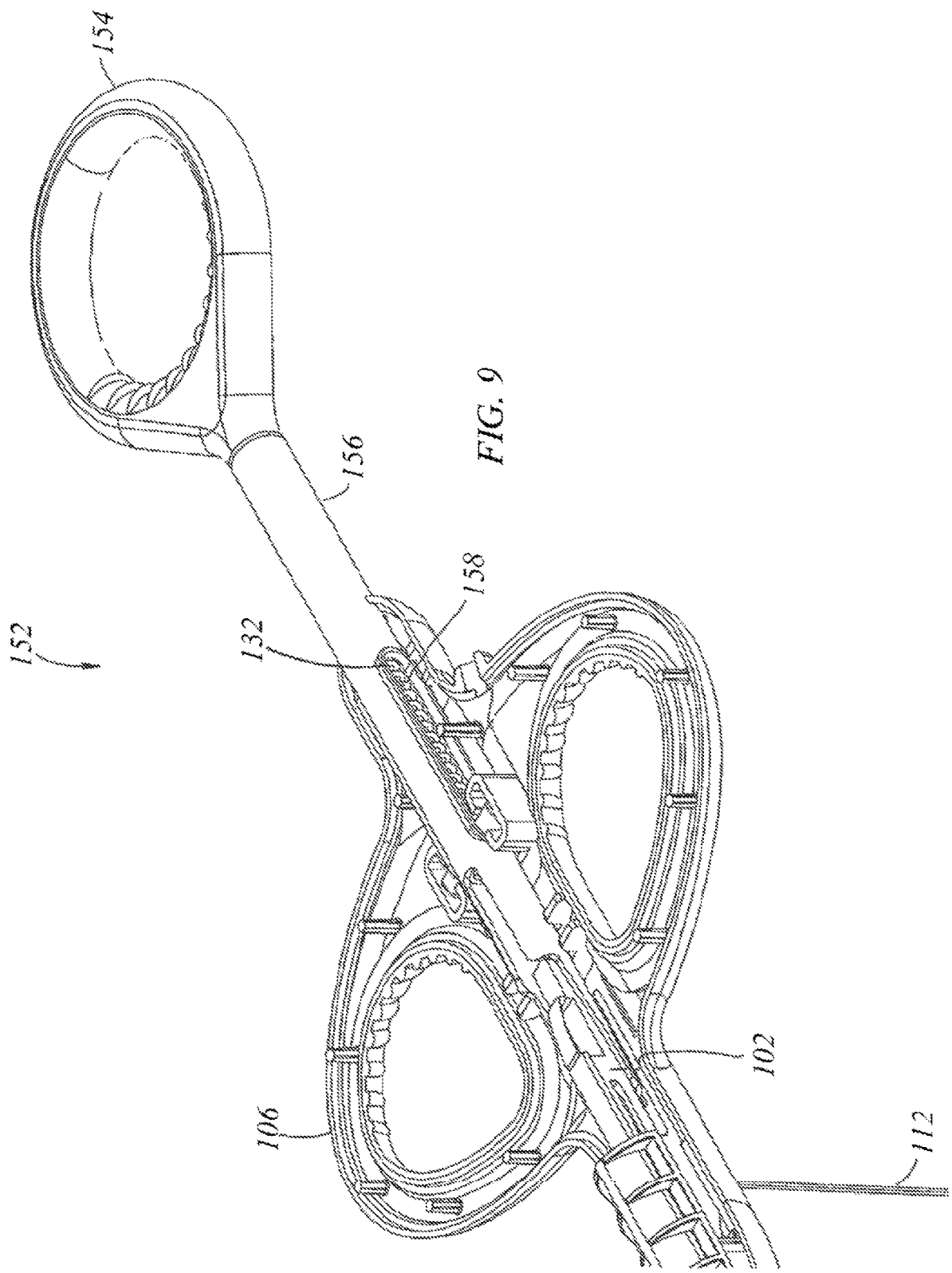
FIG. 9 is a front/top perspective view of the proximal end of the handheld suture deployment device depicted in FIG. 1A (with certain parts omitted for clarity)

As depicted in FIGS. 5B, 9 and 10, a cavity located on the lower surface of handle interface 174 is provided. This cavity mates with a catch mechanism located on the lower surface of suture cartridge interface 184. Thus, handle interface 174 is releasably retained to suture cartridge interface 184, within the housing of handle 106, due to the catch mechanism mating with the cavity. Retention of handle interface 174 can be released through operation of release button 160.

According to an embodiment, operating room loaded cartridges 122 are substantially similar in form fit and function to pre-loaded suture cartridges 120, except that operating room loaded cartridges 122 are not provided with a suture 112.

According to certain embodiments of the invention, shaft 104 has a distal end and a proximal end, as depicted in FIG. 1A. Shaft 104 generally includes lumen 134, upper clamp jaw 128, cartridge channel 172, and at least one fiber optic bundle 136. In one embodiment, shaft 104 includes two or more fiber optic bundles 136. In an embodiment, shaft 104 includes four fiber optic bundles 136.

Shaft 104 generally has a diameter that is approximately 6.5 millimeters. The diameter can be greater or less than approximately 6.5 millimeters, however, without departing from the spirit or scope of the present invention. Upper clamp jaw, or proximal tip portion, 128 is located at the distal end of shaft 104, and handle 106 is located at the proximal end. Referring to FIG. 4F, cartridge channel 172 defines an opening at the distal end of shaft 104. Cartridge channel 172 may be a keyed channel that runs for substantially the full length of shaft 104, and is substantially axially parallel to shaft 104. As a result of its profile, which generally includes two shoulders, cartridge channel 172 acts to retain suture cartridge 102.

In one embodiment, shaft 104 generally has a diameter that is less than 12 millimeters. In another embodiment, shaft 104 generally has a diameter that is less than 9 millimeters.

In one embodiment, shaft 104 generally has a tapered region 200 at the distal end of shaft 104 and a substantially uniform region extending proximally from the tapered region, as depicted in FIG. 1A. The uniform region being substantially uniformly cylindrical and the tapered region transitioning from a substantially circular end to a substantially oblong end. In one embodiment, tapered region 200 is between approximately one centimeter and ten centimeters in length. In another embodiment, tapered region 200 is between approximately two centimeters and five centimeters in length. In another embodiment, tapered region 200 is between approximately four centimeters and five centimeters in length.

In one embodiment, tapered region 200 has a substantially uniform top-to-bottom height that is between approximately one quarter of one centimeter and two centimeters. In another embodiment, tapered region 200 has a substantially uniform top-to-bottom height that is between approximately one-half-of-one centimeter and one and one-quarter-of-one centimeters. In another embodiment, tapered region 200 has a substantially uniform top-to-bottom height that is approximately 0.81 centimeters.

In one embodiment, the uniform region of shaft 104 has a substantially circular cross-section, and the substantially oblong end of tapered region 200 has a side-to-side width that is less than the diameter of the uniform region. In another embodiment, the side-to-side width of the oblong end of tapered region 200 is approximately between approximately twenty-five millimeters and two and one-half millimeters less than the diameter of the uniform region.

Lumen 134 is substantially axially parallel with both shaft 104 and cartridge channel 172, according to certain embodiments of the invention. Lumen 134 defines an opening 135 on the planar distal surface of upper clamp jaw 128 and a proximal opening in handle 106. Lumen 134 is generally substantially straight. The inner diameter of lumen 134 is generally appropriately sized to accommodate needle assembly 116 when inserted alone, and needle assembly 116 when extracted with a captured suture 112. Lumen 134 is substantially co-axial with lumen 182

According to certain embodiments of the invention, fiber optic bundles 136 are positioned within shaft 104. Each fiber optic bundle 136 generally includes two fiber optic strands. Each fiber optic bundle 136 functionally terminated at clamping plane 129, such that a light input to one of the fiber optic strands results in a reflected, or refracted optical signal that is detectable by the other fiber optic strand within a fiber optic bundle 136. Such a reflected or refracted optical signal may correspond to the nature and color of any material that is present at, or in proximity to, clamping plane 129. Fiber optic bundles 136 are operably connected through fiber optic cable assembly 108 to the leaflet capture verification (LCV) monitor 110.

As depicted in FIGS. 4A-4E and 4G-4J, lower clamp jaw 124 and upper clamp jaw 128 work cooperatively to form clamp, or bifurcated tip, 114. According to certain embodiments of the invention, clamp 114 which is generally bifurcated, low-profile, and tapered so as to perform any number of grasping functions.

Through the actuation of plunger assembly 152, lower clamp jaw 124 can be extended distally from upper clamp jaw 128, and can be retracted. When lower clamp jaw 124 is fully retracted, clamp 114 is in a closed position. In the closed position, lower clamp surface 126 contacts clamping plane 129. In the closed position, the outer surfaces of upper clamp jaw 128 and the outer surfaces of lower clamp jaw 124 are substantially coextensive. In a closed position, the outside surfaces of lower clamp jaw 124 and upper clamp jaw 128 form a substantially smooth surface such that no snagging, rough, or sharp edges or overlaps are formed. When lower clamp jaw 124 is extended, clamp 114 is in an open position. In an open position, lower clamp jaw 124, and upper clamp jaw 128 can be positioned around a piece of tissue, such as a mitral valve leaflet. Through the relative movement of lower clamp jaw 124, clamp 114 is operable to capture a valve leaflet, and needle 138 can penetrate the captured valve leaflet via lumens 134, 182.

According to certain embodiments of the invention, clamp 114 presents an oversized leaflet capture area compared to the cross-sectional area of shaft 104.

In a closed position, the outside surfaces of lower clamp jaw 124 and upper clamp jaw 128 form a substantially smooth surface, according to certain embodiments of the invention. This smooth surface can facilitate the insertion of clamp 114 into a tissue opening that is smaller than the clamp's cross-sectional area due to the elasticity of tissue over short periods of time. For the embodiments of the invention depicted in FIGS. 4A-4E and 8, the shaft diameter is approximately 85% of the maximum diameter of clamp 114. By employing this ratio of clamp-to-shaft diameters, body tissues can be stretched within their elastic limits, which permits an oversized leaflet capture area within clamp 114 as compared to the cross-sectional area of shaft 104.

An oversized leaflet capture area, as compared to the shaft's 104 cross-sectional area, is presented due to the clamping angle θ, according to certain embodiments of the invention. Clamping angle θ is the angle that clamping plane 129 makes with a horizontal plane through the centerline of shaft 104 as indicated by θ on FIG. 4C. For the embodiments of the invention depicted in FIG. 4C, clamping angle θ is approximately 120 degrees. In other embodiments of the invention, clamping angle θ is approximately between 115 degrees and 125 degrees. In other embodiments of the invention, clamping angle θ is approximately between 90 degrees and 135 degrees. In still other embodiments of the invention, clamping angle θ is approximately between 135 degrees and 155 degrees. A clamping angle that is greater than 90 degrees may result in a leaflet capture area of clamp 114 that is larger, relative to shaft's 104 cross-sectional area, than would be possible were the clamping angle 90 degrees. For a clamping angle that is approximately 120 degrees, the leaflet capture area of clamp 114 will be approximately 30% to 40% larger than if the clamping angle were 90 degrees.

In an embodiment of the present invention, a canted tip with increased clamp travel improves leaflet capture. In another embodiment of the present invention, an exchangeable cartridge improves the simplicity and reliability of suture deployment. In another embodiment of the present invention, a suture deployment and manipulator mechanism is integrated with a visualization and verification system to deploy sutures within a suture zone of a valve leaflet.

According to certain embodiments of the invention, clamp 114 is a low profile tapered tip grasping device. The shape of the tapered tip facilitates leaflet capture by providing a large surface area for leaflet capture, relative to the diameter of the shaft. In one embodiment, the surface area for leaflet capture is between 30% and 50% greater than the cross-sectional area of the shaft 104. In another embodiment, the surface area for leaflet capture is between 20% and 100% greater than the cross-sectional area of the shaft 104.

According to certain embodiments of the invention, clamp 114 is a low profile canted tip grasping device. Clamp 114 can be canted in any number of directions. Generally, however, the canted tip is canted up, as depicted in FIGS. 54-55. A large surface area of the canted tip, relative to the diameter of the shaft, facilitates leaflet capture.

A large leaflet capture area can provide a surgeon with certain advantages as compared to a smaller leaflet capture area. These advantages include improved ability to capture a leaflet that may be damaged or enlarged and a leaflet capture that is more stable. Greater stability in turn can provide a surgeon enhanced control of a captured leaflet.

According to an embodiment of the invention, the maximum linear travel of lower clamp jaw 124 in relation to upper clamp jaw 128 is between approximately one and five centimeters. According to another embodiment of the invention, the maximum linear travel of lower clamp jaw 124 in relation to upper clamp jaw 128 is between approximately two and three centimeters.

According to certain embodiments of the invention, handle 106 is formed to be manipulated by an operator. Operator may be, for example, a surgeon, or the controllable device-interfacing end of a robotic system. In one embodiment, handle 106 is adapted to be grasped by the index and middle finger of a surgeon. Shaft 104 extends from the distal end of handle 106, and plunger assembly 152 is retained in the proximal end. As depicted in FIG. 9, structure is provided within handle 106 to retain plunger assembly 152 such that plunger assembly 152 is permitted to engage with suture cartridge 102, and to translate in both the distal and proximal directions. Suitable structure for retaining plunger assembly 152 within handle 106 include, for example, a pin and shackle arrangement, a retaining collar, a boss within a groove, and the like. As depicted in FIGS. 9 and 11, a pin and retaining shackle arrangement is employed, with the pin biased against spring 158 within slot 132 of plunger shaft 156, in order to permit translational movement of plunger assembly 152. Release button 160 is located on the bottom surface of handle 106, as depicted in FIG. 10. Release button 160 transfers an operator's input to the retaining structure of handle interface 174 in order to uncouple suture cartridge 102 from plunger assembly 152. A track may also be provided on the top surface of handle 106 that accepts needle carriage 144. Markings are provided on the top surface of the handle, adjacent to the track, to aid an operator in positioning needle carriage 144.

As depicted in FIGS. 9 and 11, plunger assembly 152 generally includes plunger thumb handle 154, plunger shaft 156, suture cartridge interface 184 and spring 158, according to certain embodiments of the invention. Plunger thumb handle 154 is formed to be grasped by the thumb of an operator and is provided on the proximal end of plunger assembly 152. Suture cartridge interface 184 is provided on the distal end of plunger assembly 152 and is formed to engage and releasably retain suture cartridges 102. Intermediate suture cartridge interface 184 and plunger thumb handle 154 is plunger shaft 156. Slot 132 is located along a portion of the length of plunger shaft 156. Spring 158 is located within slot 132 of plunger shaft 156, and in cooperation with a pin and retaining structure within handle 106, serves to bias plunger assembly 152 to a proximal position relative to handle 106. As a result of the releasable retention between suture cartridge interface 184 and suture cartridges 102, the biasing action of spring 158 is translated to suture cartridge 102. This biasing action favors retention of clamp 114 in a closed or grasping position. Biasing of plunger 152 in this manner facilitates slow and incremental clamp extension and contraction.

In one embodiment, spring 158 favors retention of clamp 114 in a closed or grasping position with a force in the range of approximately zero pounds per inch of travel to twenty pounds per inch of travel. In one embodiment, spring 158 favors retention of clamp 114 in a closed or grasping position with a force of approximately five pounds per inch of travel.

As illustrated in FIG. 7, certain embodiments of needle assembly 116 generally include needle 138, needle handle 140, and needle head, or needle end, 146. Needle 138 is formed from 304 stainless steel wire or other suitable material, is generally circular in shape, and has a distal end and a proximal end. Needle end 146 is provided on the distal end of needle 138 and needle handle 140 is provided on the proximal end of needle 138. Needle end 146 is flattened and a notch 148 is provided to create hook 150. Notch 148 is equal to, or greater than, the diameter of suture 112. Needle handle 140 generally includes finger tabs 142, and needle carriage 144. Needle carriage 144 is permitted to travel along a track that is provided within the top housing of handle 106. Such travel permits needle 138 from moving from a starting position (needle end 146 is within upper clamp jaw 128, as depicted in FIG. 51) to a fully extended position (needle hook 150 within lumen 182). Needle carriage 144 is also permitted to travel in a proximal direction along the track, such proximal travel extending to a position where needle carriage 144 disengages from the track, and needle assembly 116 is removed from the handheld device 118. Markings provided adjacent to the track aid an operator in selecting the correct position of the needle carriage 144 in order to achieve a desired position of needle 138. A detent is also provided to aid in locating the starting position of needle assembly 138. Finger tabs 142 fan out from the centerline of needle assembly 116 and in so doing, act to prevent needle carriage 144 from being inadvertently displaced. In order for an operator to displace needle carriage 144, an operator must first grasp and press finger tabs 142 together, and then needle carriage 144 can be displaced along the track. In one embodiment, a biasing member opposes the movement of needle carriage 144 to a distal position.

According to certain embodiments of the invention, fiber optic cable assembly 108 generally includes fiber optic cable 166 and strain relief 164. Fiber optic cable 166 generally includes four (4) fiber optic bundles 136 that run from the distal surface of upper clamp jaw 128 to the leaflet capture verification (LCV) monitor 110. The four (4) fiber optic bundles 136 are bundled together within fiber optic cable 166 and are jacketed with a medical grade PVC cover, or other suitable covering material. Strain relief 164 is provided at the interface between fiber optic cable 166 and leaflet capture verification (LCV) monitor 110 as depicted in FIG. 12.

According to certain embodiments of the invention, fiber optic cable assembly 108 is at least two-hundred-and-twenty centimeters long. For these embodiments, in an operating room setting, LCV monitor 110 can be placed outside of the sterile field, which results in the option to package device 100 in such a manner that LCV monitor 110 need not be sterilized.

According to another embodiment, a fiber optic connector (not depicted) can be used to operably connect fiber optic cable assembly 108 to LCV monitor 110. The use of such a connector permits the sterilization and sterile packaging of the handheld device 118 and fiber optic cable assembly 108, while the LCV monitor 110 can be separately packaged in an unsterilized condition. In an operating room setting, handheld device 118 and fiber optic cable assembly 108 can be introduced into the sterile field, while LCV monitor 110 can be placed outside of the sterile field, within surgical line-of-sight of a TEE monitor, and the fiber optic connector used to operably connect LCV monitor 110 and fiber optic cable assembly 108.

Figure 13:
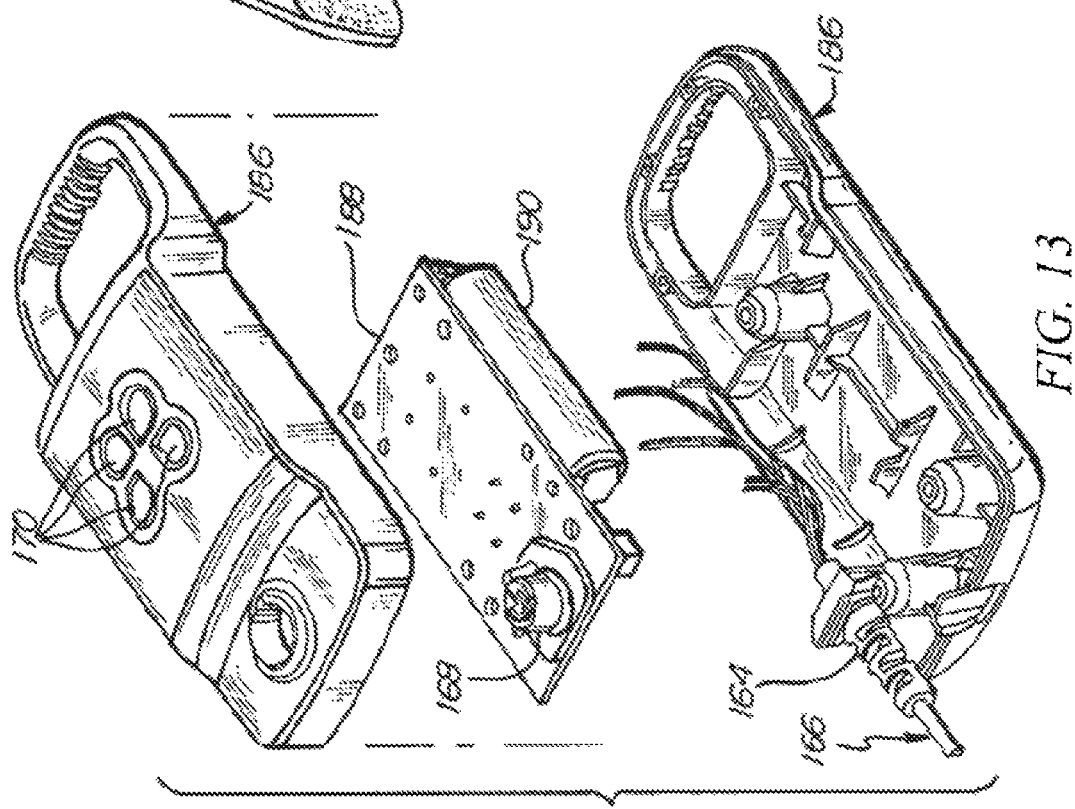
FIG. 13 is an exploded front/top perspective view of the fiber optic cable assembly depicted in FIG. 12.

As depicted in FIGS. 12 and 13, leaflet capture verification (LCV) monitor 110 generally includes power button 168, four (4) LED displays 170, housing 186, circuit board 188, and an internal power supply 190, according to certain embodiments of the invention. Housing 186 includes an integrated loop which is adapted to be securely clipped or hung such that the LED displays 170 of LCV monitor 110 can be placed within surgical line-of-sight of a TEE monitor. Disposed on circuit board 188 is internal power supply 190, power button 168 and a light source, such as an LED. For other embodiments, more than one light source can be used. Circuit board 188, internal power supply 190, power button 168, and the light source are all operably connected in a manner familiar to those who are skilled in the art. Activation of power button 168 results in the light source being turned on/off. Four sets of fiber optic bundles 136 enter housing 186 via fiber optic cable 166 and strain relief 164. Each fiber optic bundle 136 generally includes two fiber optic strands. For each fiber optic bundle 136, one of the fiber optic strands is operably connected to the light source, while the other fiber optic strand is operably connected to one of the four (4) LED displays 170. Power button 168, the four (4) LED displays 170, circuit board 188, the an internal power supply 190, and the light source(s) are all contained within housing 186. The four (4) LED displays 170 are visible to an operator from outside of housing 186, and power button 168 is operable from outside of housing 186.

In operation, device 100 can be used to attach a suture within the suture target zone 194 of a valve leaflet, as depicted in FIG. 43. To accomplish this, the device 100 may employ a visualization and verification system. The visualization and verification system integrates external transesophageal echocardiography (TEE) to visualize a valve leaflet in multiple axes and fiber optics to verify leaflet capture. In an embodiment, suture target zone 194 is generally two millimeters from the leading (prolapsing) edge of the leaflet. In another embodiment, suture target zone 194 is one millimeter wide and has a centerline that is located two millimeters from the leading (prolapsing) edge of the leaflet. In another embodiment, suture target zone 194 is one millimeter wide and has a centerline that is located three millimeters from the leading (prolapsing) edge of the leaflet. In another embodiment, suture target zone 194 is one millimeter wide and has a centerline that is located four millimeters from the leading (prolapsing) edge of the leaflet. In another embodiment, suture target zone 194 is greater than one millimeter wide and has a centerline that is located between two millimeters and five millimeters from the leading (prolapsing) edge of the leaflet. In another embodiment, suture target zone 194 is less than one millimeter wide and has a centerline that is located between two millimeters and five millimeters from the leading (prolapsing) edge of the leaflet. In one embodiment, the fiber optics include a leaflet capture verification (LCV) monitor 110 and a fiber optic cable assembly 108, as depicted in FIGS. 1A and 12.

Referring to FIGS. 4E and 4F, in an embodiment, fiber optic bundles 136 terminate at upper clamp jaw 128 in a configuration that surrounds lumen opening 135. In another embodiment, fiber optic bundles 136 terminate at upper clamp jaw 128 in a configuration that is near lumen opening 135. Those skilled in the art will realize that many variations in the configuration of the placement of the terminations of fiber optic bundles 136 at clamping plane 129 are possible in order to meet the spirit and scope of the present invention. The identification of certain configurations is not intended to exclude others which are not identified, but are provided as examples of possible configurations.

Fiber optic bundles 136 are operably connected through fiber optic cable assembly 108 to the leaflet capture verification (LCV) monitor 110, according to certain embodiments of the invention. When a valve leaflet has been grasped in clamp 114, the LCV monitor 110 displays a light transmission that corresponds to the configuration of fiber optic bundles 136 at clamping plane 129, and which identifies whether the valve leaflet is properly captured in clamp 114.

According to certain embodiments, the present invention can be used with robotic multi-axis control and manipulation of the device. Proximal control of the instrument can be achieved with a system interface comprised of the necessary electrical and electro-mechanical interconnects to actuate the mechanical operations of the instrument. According to an embodiment, the distal tip of the device can have a rigid shaft. According to another embodiment, the distal end of the device can have an articulating, multiple axis tip for orientation of the clamp and suture delivery.

According to certain embodiments of the invention, the movable tip typically remains in the closed position during thoracoscopic insertion and manipulation of the handheld device 118. As desired by an operator, plunger 152 can be manipulated to separate the two portions of the moveable tip, as depicted in, for example, FIGS. 4D-4E, 4G-4J and 49.

According to certain embodiments of the invention, clamp 114 is biased to a closed position through the use of spring 158, or other biasing member. A clamp that is biased closed aids in leaflet capture verification as it can provide a surgeon with a distinctive tactile feedback when a leaflet has been captured, as compared to when the result is a failed or partial leaflet capture.

In practice, certain embodiments of the present invention can be used to attach a suture to the suture zone of a valve leaflet in a beating heart, as depicted in FIGS. 14-42 and 46-48. In one embodiment, the apex of the left ventricle is accessed. Such access can be obtained by thoracotomy or other suitable surgical technique. Shaft 104 of the handheld suture deployment device 118 is then inserted through the apex of the heart into the left ventricle using transesophageal echocardiography (TEE) to guide the surgeon. A purse string suture at the site of left ventricular apical access can be used to control blood loss.

Figure 15:
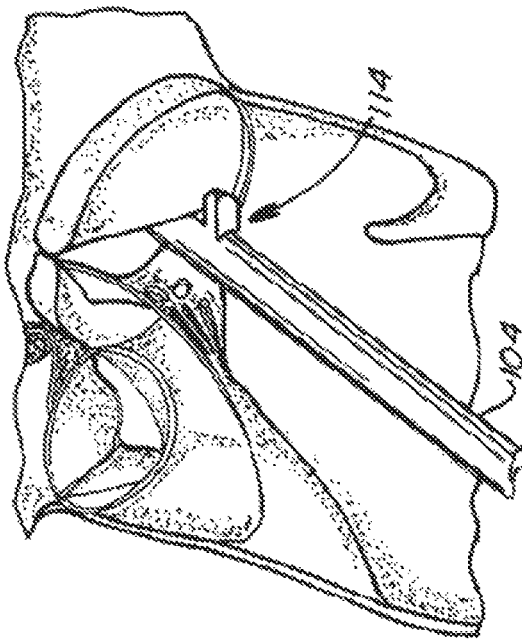
FIG. 15 is a front/bottom perspective view of a mitral valve leaflet in need of repair, and the distal end of the handheld suture deployment device depicted in FIG. 1A.
Figure 14:
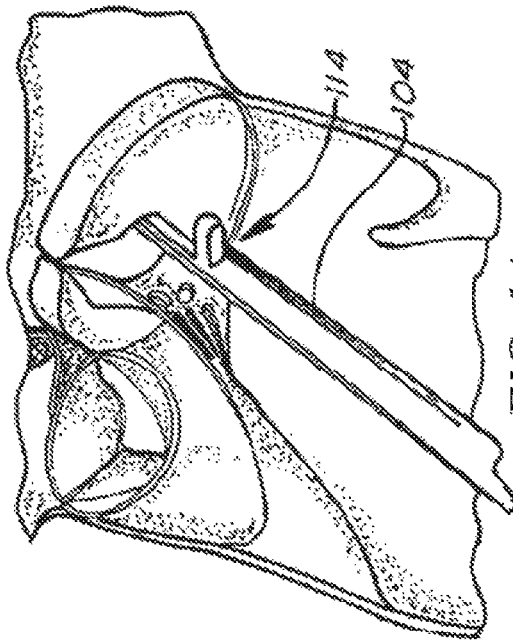
FIG. 14 is a front/bottom perspective view of a mitral valve leaflet in need of repair, and the distal end of the handheld suture deployment device depicted in FIG. 1A.
Figure 16:
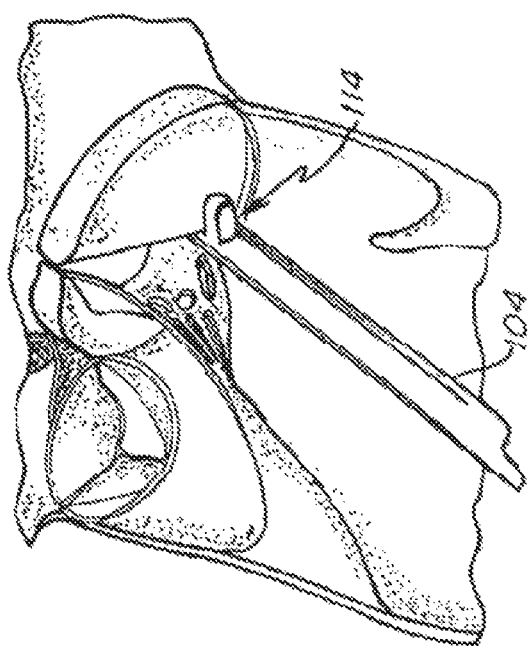
FIG. 16 is a front/bottom perspective view of a mitral valve leaflet in need of repair captured by the clamp of the handheld suture deployment device depicted in FIG. 1A.
Figure 19:
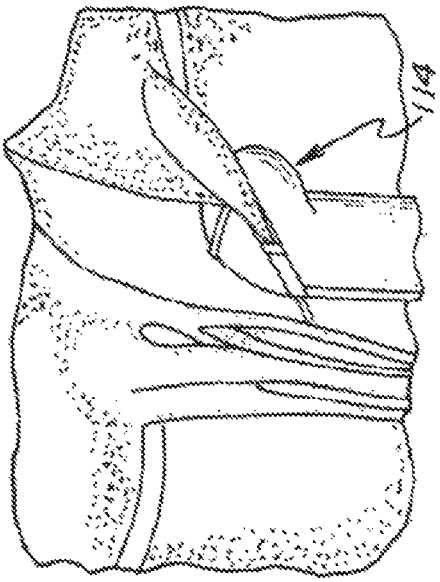
FIG. 19 is a side/bottom perspective view of a mitral valve leaflet captured by the clamp of the handheld suture deployment device depicted in FIG. 1A.
Figure 21:
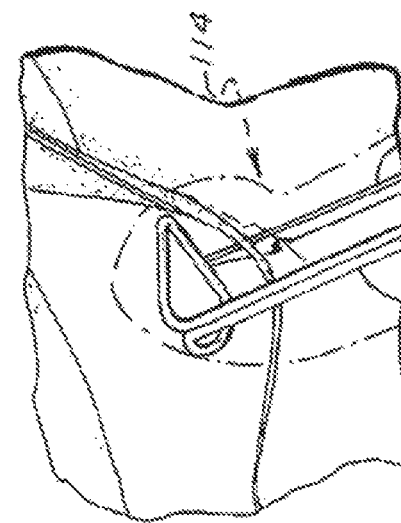
FIG. 21 is a side/bottom perspective view of a mitral valve leaflet captured by the clamp of the handheld suture deployment device depicted in FIG. 1A, with the clamp shown in phantom.
Figure 22:
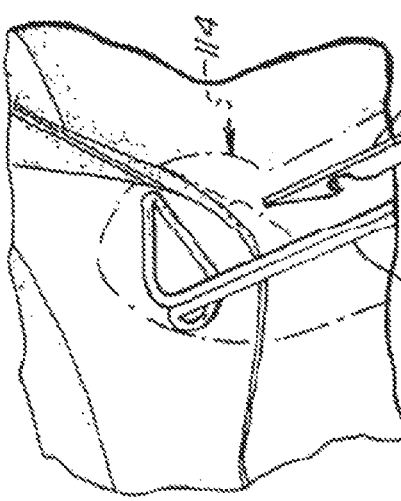
FIG. 22 is a side/bottom perspective view of a mitral valve leaflet captured by the clamp of the handheld suture deployment device depicted in FIG. 1A, with the clamp shown in phantom.
Figure 23:
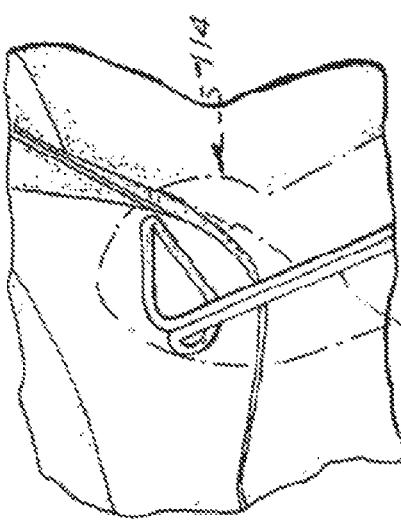
FIG. 23 is a side/bottom perspective view of a mitral valve leaflet in need of repair captured by the clamp of the handheld suture deployment device depicted in FIG. 1A, with the clamp shown in phantom.
Figure 24:
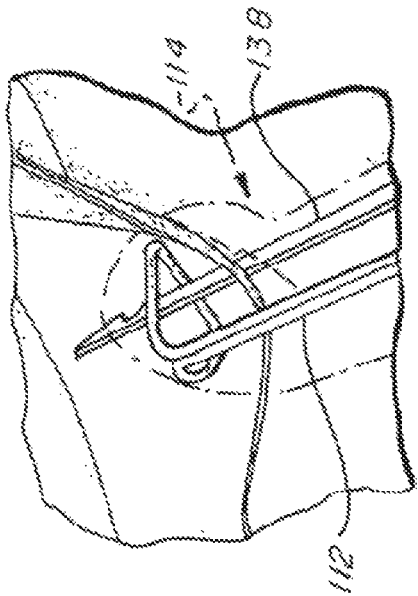
FIG. 24 is a side/bottom perspective view of a mitral valve leaflet in need of repair captured by the clamp of the handheld suture deployment device depicted in FIG. 1A, with the clamp shown in phantom.

As depicted in FIGS. 14-16, while the heart is beating, the movable tip of the platform is used to guide the capture of a flailing leaflet as clamp 114 is closed. A surgeon can use external transesophageal echocardiography to guide the placement of the movable tip relative to a target leaflet. Through further use of transesophageal echocardiography, as well as the tactile feel of plunger 152, and LCV monitor 110, a surgeon can verify leaflet capture.

Figure 18:
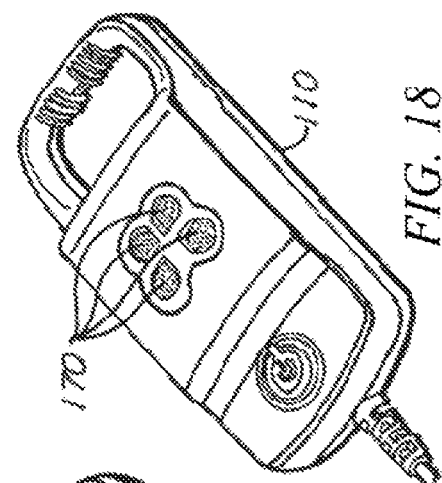
FIG. 18 is a front perspective view of the leaflet capture verification monitor depicted in FIG. 1A.
Figure 17:
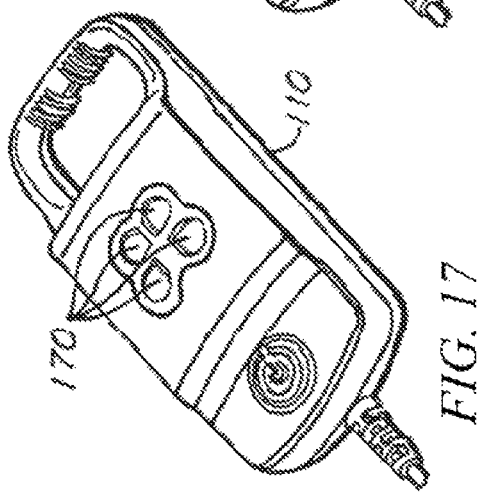
FIG. 17 is a front perspective view of the leaflet capture verification monitor depicted in FIG. 1A.
Figure 20:
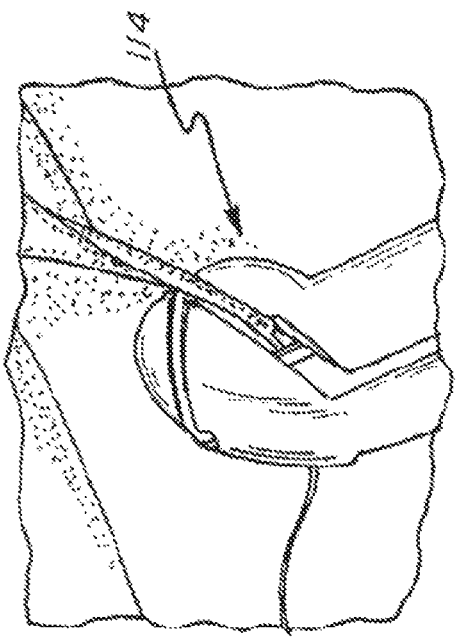
FIG. 20 is a side/bottom perspective view of a mitral valve leaflet captured by the clamp of the handheld suture deployment device depicted in FIG. 1A.

Once the leaflet is captured, a surgeon can verify capture by examining the leaflet capture verification (LCV) monitor 110 to assure leaflet tissue is present. In an embodiment, the four LED displays 170 of the LCV monitor 110 present red when blood is present at clamping plane 129, as depicted in FIG. 17, while a display of four white lights indicates that the tissue has been fully captured by the movable tip, as depicted in FIG. 18.

Figure 25:
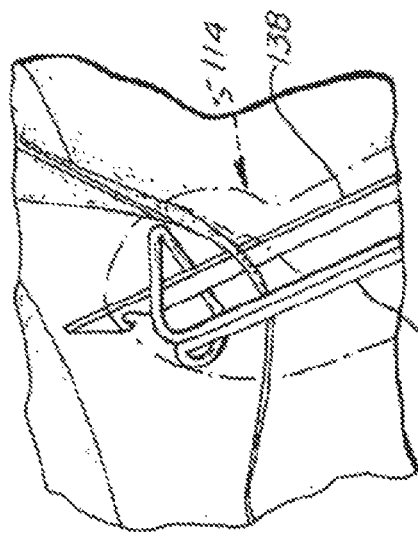
FIG. 25 is a side/bottom perspective view of a mitral valve leaflet in need of repair captured by the clamp of the handheld suture deployment device depicted in FIG. 1A, with the clamp shown in phantom.
Figure 30:
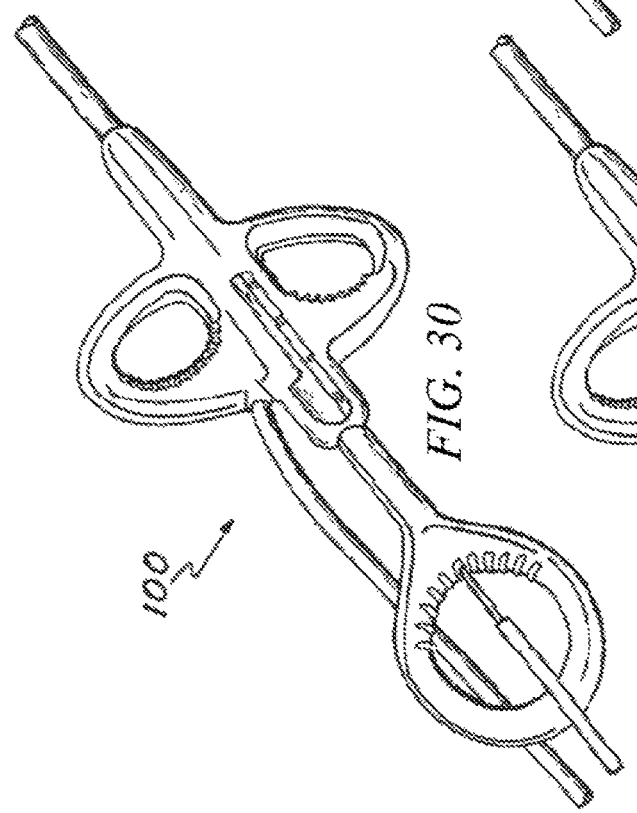
FIG. 30 is a top/rear perspective view of the handheld suture deployment device depicted in FIG. 1A and the needle assembly depicted in FIG. 1A partially retracted from the handheld suture deployment device.
Figure 31:
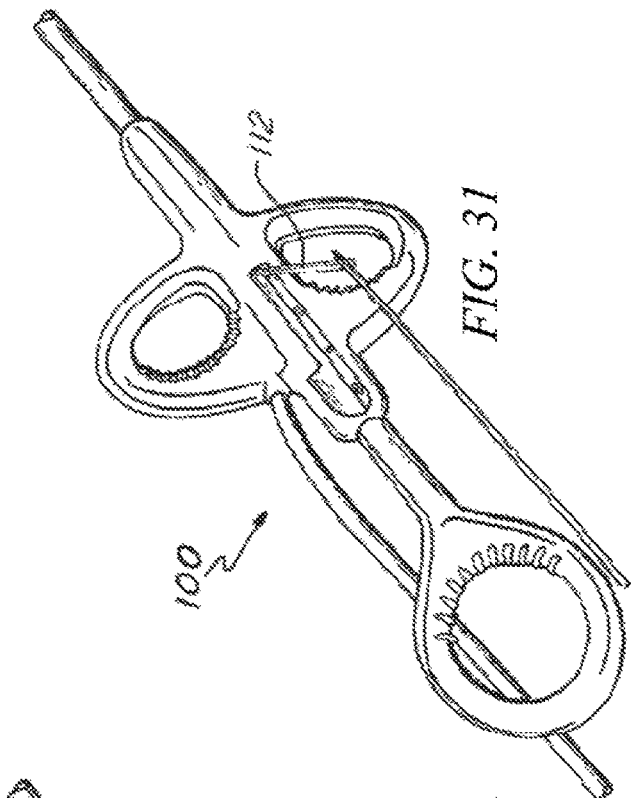
FIG. 31 is a top/rear perspective view of the handheld suture deployment device depicted in FIG. 1A, the needle assembly depicted in FIG. 1A retracted from the handheld suture deployment device, and the suture depicted in FIG. 1A.
Figure 32:
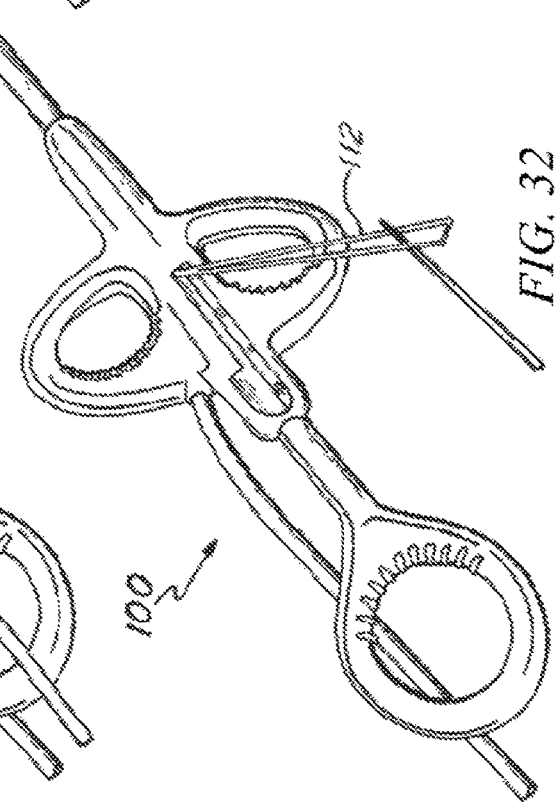
FIG. 32 is a top/rear perspective view of the handheld suture deployment device depicted in FIG. 1A, the needle assembly depicted in FIG. 1A retracted from the handheld suture deployment device, and the suture depicted in FIG. 1A.
Figure 33:
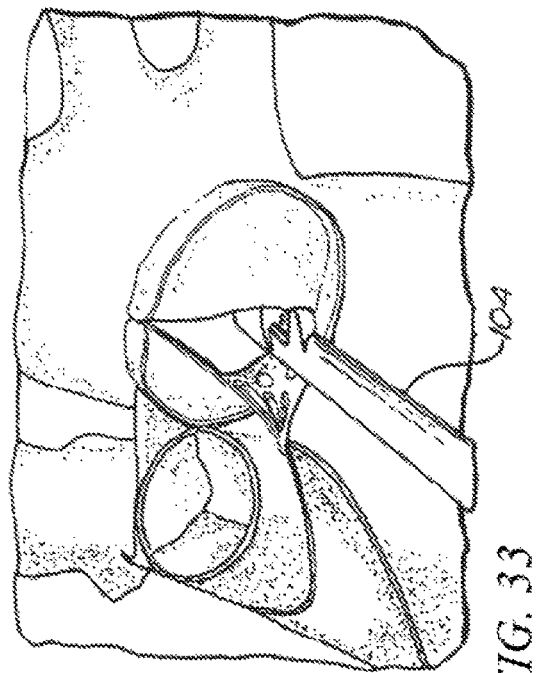
FIG. 33 is a front/bottom perspective view of a mitral valve leaflet in need of repair, and the distal end of the handheld suture deployment device depicted in FIG. 1A partially retracted from the heart chamber.
Figure 35:
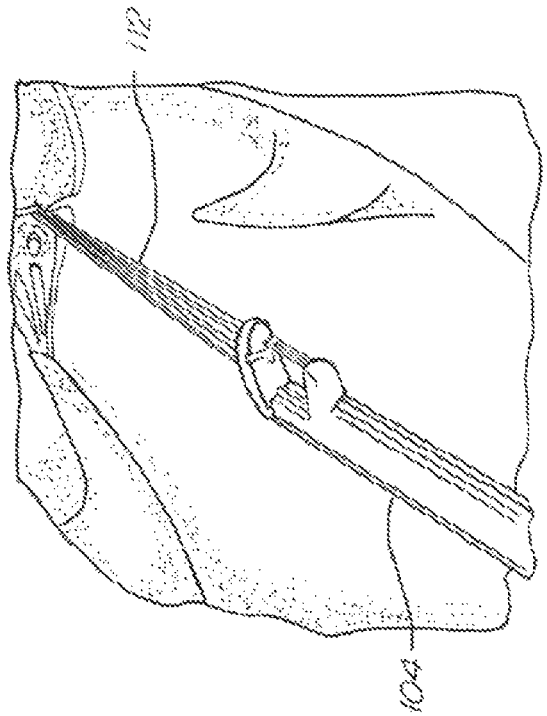
FIG. 35 is a front/bottom perspective view of a mitral valve leaflet in need of repair, and the distal end of the handheld suture deployment device depicted in FIG. 1A partially retracted from the heart chamber.
Figure 38:
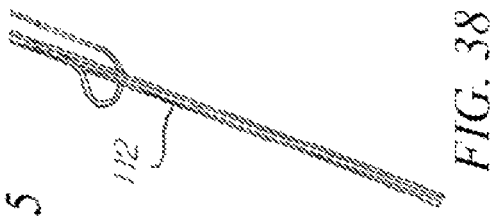
FIG. 38 is an perspective view of the loop and non-loop ends of the suture depicted in FIG. 1A.
Figure 34:
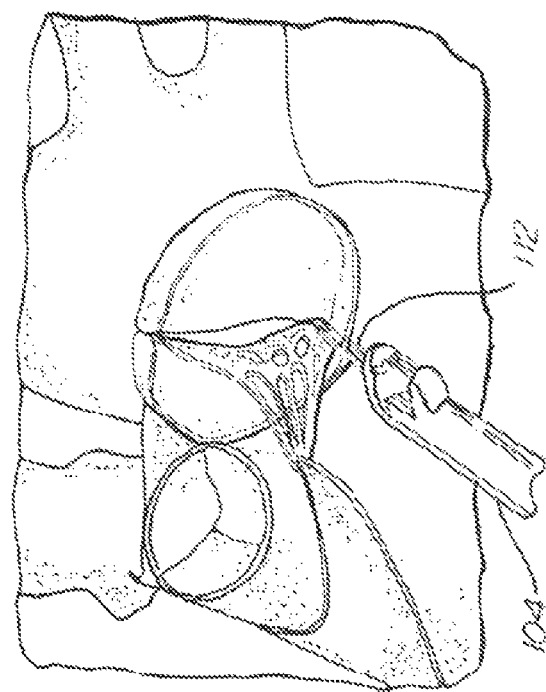
FIG. 34 is a front/bottom perspective view of a mitral valve leaflet in need of repair, and the distal end of the handheld suture deployment device depicted in FIG. 1A partially retracted from the heart chamber.
Figure 37:
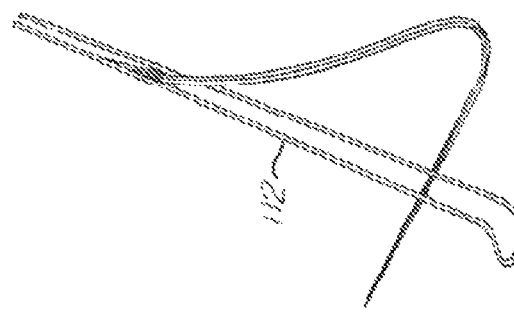
FIG. 37 is an perspective view of the loop and non-loop ends of the suture depicted in FIG. 1A.
Figure 36:
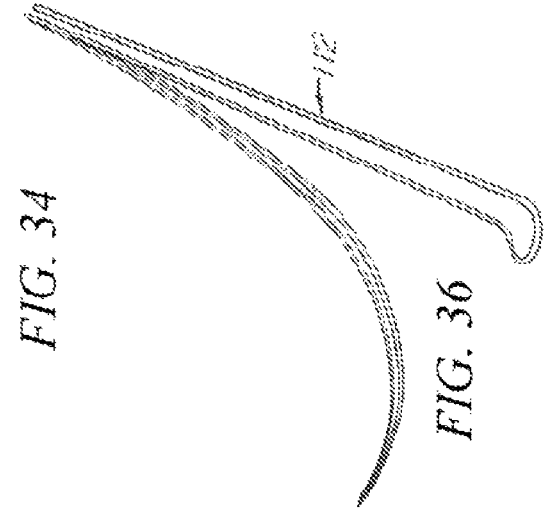
FIG. 36 is an perspective view of the loop and non-loop ends of the suture depicted in FIG. 1A.
Figure 40:
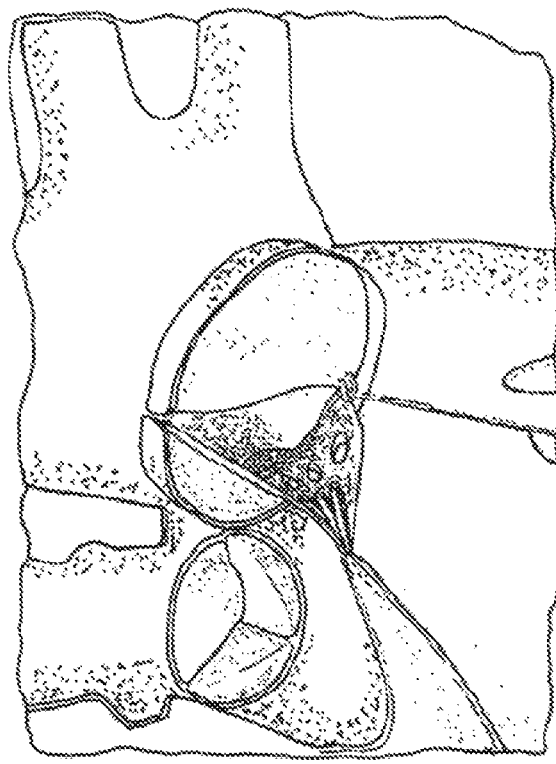
FIG. 40 is a front/bottom perspective view of a mitral valve leaflet in need of repair, and a loose girth hitch on the leaflet.
Figure 39:
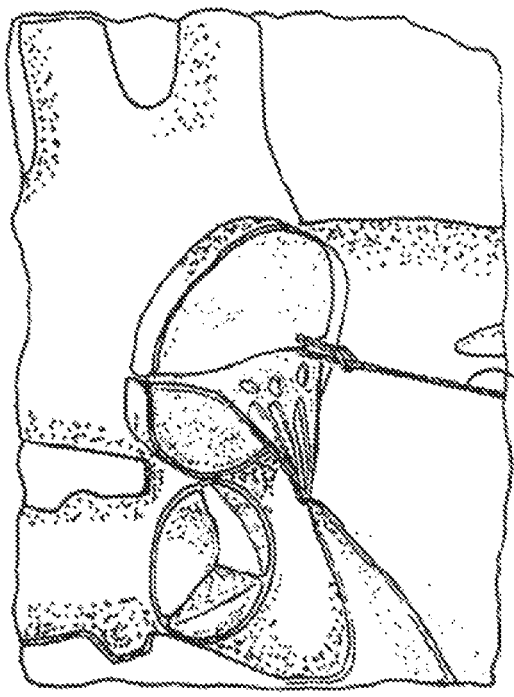
FIG. 39 is a front/bottom perspective view of a mitral valve leaflet in need of repair, and a loose girth hitch on the leaflet.
Figure 41:
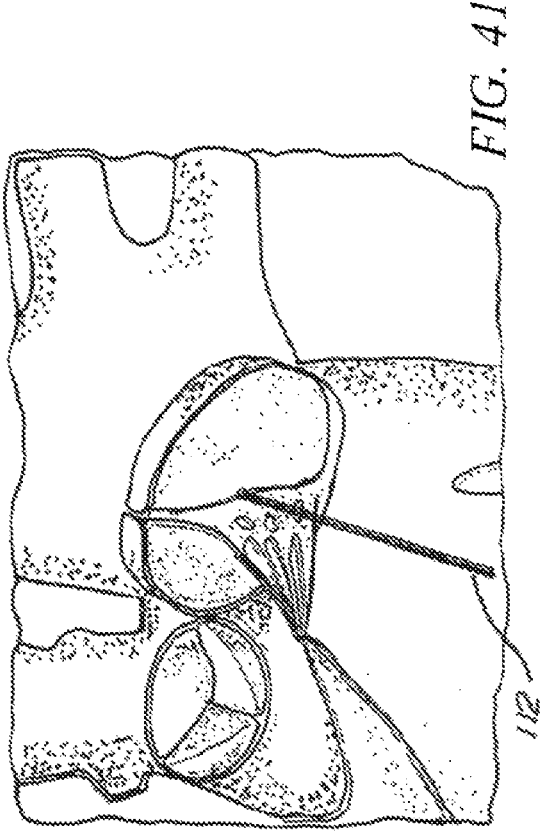
FIG. 41 is a front/bottom perspective view of a mitral valve leaflet in need of repair, and an adjusted girth hitch on the leaflet.

In one embodiment, an operator can penetrate the leaflet with needle 138 and retrieve secured suture 112 from the lower clamp jaw 124 by engaging needle assembly 116. First, needle 138 is advanced by guiding the needle assembly carriage 144 forward, or toward the distal end of the platform as depicted in FIGS. 19-24 (the movable tip is illustrated in phantom in FIGS. 21-24 so that the advancement of needle 138 can be visibly depicted). Once needle 116 is fully advanced, the needle assembly is rotated to engage suture 112 as depicted in FIGS. 25-27 (the movable tip is illustrated in phantom in FIGS. 25-27 so that the rotation of needle 138 can be visibly depicted). The suture loop is retrieved by retracting (movement is in the proximal direction) the needle assembly entirely from handheld device 118 as depicted in FIGS. 28-32. The handheld device 118 can then be extracted from the ventricle while maintaining control of both ends of the suture as depicted in FIGS. 33-35.

In another embodiment, no rotation of needle 138 is necessary. A surgeon advances needle 138 by guiding the needle assembly carriage 144 forward, or toward the distal end of the platform as depicted in FIG. 8C. Once needle 116 is fully advanced, needle hook 150 engages with suture 112, as depicted in FIG. 8, when needle assembly carriage 144 is retracted as depicted in FIG. 8D. Needle hook 150 can advance past suture 112 without dislodging suture 112 from groove 162 because suture retention system 130 acts to retain suture 112 as threaded on and within suture cartridge 102. Suture retention system 130 releases suture 112 once needle 138 has been is fully advanced.

In embodiments of the invention that have cutout 161, handheld device 118 can be extracted with clamp 114 in a closed position. This is because cutout 161 permits suture 112 to be clear of clamp 144 after the suture loop is retrieved from handheld device 118. Extracting handheld device 118 with clamp 114 in a closed position facilitates the extraction.

In one embodiment, the non-loop end of the suture 112 is passed through the loop to create a girth hitch on the leaflet as depicted in FIGS. 36-41 and 47-48. The girth hitch provides for distributed stress on the leaflet with two suture legs and avoids the need for a knot at the site of leaflet capture.

In one embodiment, a surgeon can thread one of the free ends of the suture 112 into an operating-room loaded cartridge 122 and repeat the capture process on an adjacent (non-flailing) leaflet to create leaflet plication or what is commonly known as the Alfieri stitch.

In other embodiments, the handheld device 118 can be adapted to form different types of knots or stitches that can be used for mitral valve repair. This can be accomplished through changes to one or more of: the relative location of the needle within the shaft; the relative orientation of the suture within the distal tip; the configuration of the suture within the distal tip; the relative orientation of the needle hook; the addition of one or more needle ends to the needle assembly; and the relative locations of multiple needle ends within the shaft.

At this stage, the surgeon can visualize the function of the mitral valve leaflet using TEE as depicted in FIG. 42. An operator can then incrementally adjust the tension on the suture, while monitoring the corresponding mitral valve regurgitation through the use of TEE, to allow for ideal coaptation of the mitral valve leaflets and consequently a reduction or elimination of MR. If the competency of the mitral valve is satisfactory, the suture can be secured to a suitable location. Suitable locations for this purpose can include the epicardium, a papillary muscle and other like locations. Securing the suture can be accomplished using a standard surgical knot and pledget.

In one embodiment of the present invention, the process can be repeated by removing exchangeable cartridge 102 from the handheld device 118 and replacing it with a pre-loaded suture cartridge 120. In another embodiment, the process can be repeated by removing exchangeable cartridge 102 from the handheld device 118 and threading a suture 112 into operating room loaded cartridge 122 which can then be installed into handheld device 118.

The invention claimed is:

1. A method of repairing a heart valve in a beating heart of a patient, comprising:
   percutaneously inserting a suture attachment device including a capture assembly having a proximal clamping jaw and a distal clamping jaw carrying a suture under tension into a beating heart of a patient;
   operating a jaw actuator on a handle assembly of the suture attachment device to create a space between the proximal clamping jaw and the distal clamping jaw;
   positioning the capture assembly such that the valve leaflet is in the space between the proximal clamping jaw and the distal clamping jaw;
   clamping the valve leaflet between the proximal clamping jaw and the distal clamping jaw; and
   operating a needle actuator on the handle assembly to actuate a needle to retrieve the suture carried under tension on the distal clamping jaw across a path of travel of the needle to insert the suture through the valve leaflet.

2. The method of claim 1, wherein the proximal clamping jaw and distal clamping jaw are each angled relative to a distal end of a generally cylindrical shaft.

3. The method of claim 1, wherein the capture assembly includes a suture channel that extends around an outer perimeter surface of the capture assembly.

4. The method of claim 1, wherein the distal clamping jaw is biased towards a closed position with respect to the proximal clamping jaw.

5. The method of claim 1, wherein the capture assembly further includes a slideable shaft connected to the distal clamping jaw.

6. The method of claim 5, wherein operating the jaw actuator moves the distal clamping jaw with respect to the proximal clamping jaw by sliding the slideable shaft.

7. The method of claim 6, wherein operating the jaw actuator moves the distal clamping jaw by longitudinal movement of the jaw actuator.

8. The method of claim 1, wherein a clamping face of the distal clamping jaw includes a plurality of ridges configured to enhance retention of the leaflet between the distal clamping jaw and the proximal clamping jaw.

9. The method of claim 1, further comprising confirming capture of a valve leaflet between the proximal clamping jaw and the distal clamping jaw with one or more fiber optic cables extending from the handle assembly to the proximal clamping jaw at one or more openings on a clamping face of the proximal clamping jaw.

10. The method of claim 1, further comprising a needle release disposed at the handle assembly, the needle release configured to prevent the needle from being inadvertently displaced.

11. A method of repairing a heart valve in a beating heart of a patient, comprising:
    percutaneously inserting a suture attachment device into a beating heart of a patient;
    positioning a suture attachment assembly of the suture attachment device adjacent a valve leaflet of the heart valve;
    creating a space between a proximal clamping jaw and a distal clamping jaw of the suture attachment assembly, the distal clamping jaw carrying a suture under tension;
    positioning the suture attachment assembly such that the valve leaflet is in the space between the proximal clamping jaw and the distal clamping jaw;
    clamping the valve leaflet between the proximal clamping jaw and the distal clamping jaw; and
    actuating a needle to retrieve the suture carried under tension on the distal clamping jaw across a path of travel of the needle to insert the suture through the valve leaflet.

12. The method of claim 11, wherein the proximal clamping jaw and distal clamping jaw are each angled relative to a distal end of a device shaft.

13. The method of claim 11, wherein the suture attachment assembly includes a suture channel that extends around an outer perimeter surface of the suture attachment assembly.

14. The method of claim 11, wherein the distal clamping jaw is biased towards a closed position with respect to the proximal clamping jaw.

15. The method of claim 11, wherein creating a space between the proximal clamping jaw and the distal clamping jaw comprises longitudinally sliding the distal clamping jaw by longitudinal movement of a jaw actuator.

16. The method of claim 11, wherein a clamping face of the distal clamping jaw includes a plurality of ridges configured to enhance retention of the leaflet between the distal clamping jaw and the proximal clamping jaw.

17. The method of claim 11, further comprising confirming capture of a valve leaflet between the proximal clamping jaw and the distal clamping jaw with one or more fiber optic cables extending from a control handle to one or more openings on a clamping face of the proximal clamping jaw.

18. The method of claim 11, further comprising a needle selectively slideable within a device shaft with a needle actuator.

19. The method of claim 18, further comprising a needle release disposed at a control handle, the needle release configured to prevent the needle from being inadvertently displaced.

20. The method of claim 11, further comprising a suture configured to be retained on the distal clamping jaw for retrieval by the needle and a suture tensioning mechanism disposed at a control handle, the suture tensioning mechanism configured to enable the suture to be retained on the distal clamping jaw under tension.

* * * * *